United States Patent
Iijima et al.

(10) Patent No.: US 11,230,709 B2
(45) Date of Patent: Jan. 25, 2022

(54) THERAPEUTIC DRUG FOR ALPORT'S SYNDROME

(71) Applicants: DAIICHI SANKYO COMPANY, LIMITED, Tokyo (JP); NATIONAL UNIVERSITY CORPORATION KOBE UNIVERSITY, Hyogo (JP)

(72) Inventors: Kazumoto Iijima, Hyogo (JP); Kandai Nozu, Hyogo (JP); Akemi Shono, Hyogo (JP); Makoto Koizumi, Tokyo (JP); Yoshiyuki Onishi, Tokyo (JP); Kiyosumi Takaishi, Tokyo (JP); Tomomi Adachi, Tokyo (JP)

(73) Assignees: NATIONAL UNIVERSITY CORPORATION KOBE UNIVERSITY, Hyogo (JP); DAIICHI SANKYO COMPANY LIMITED, Tokyo (JP)

( * ) Notice: Subject to any disclaimer, the term of this patent is extended or adjusted under 35 U.S.C. 154(b) by 0 days.

(21) Appl. No.: 16/467,224

(22) PCT Filed: Dec. 25, 2017

(86) PCT No.: PCT/JP2017/046304
§ 371 (c)(1),
(2) Date: Jun. 6, 2019

(87) PCT Pub. No.: WO2018/123925
PCT Pub. Date: Jul. 5, 2018

(65) Prior Publication Data
US 2020/0080080 A1   Mar. 12, 2020

(30) Foreign Application Priority Data

Dec. 28, 2016 (JP) .............................. JP2016-254906
Apr. 10, 2017 (JP) .............................. JP2017-077374

(51) Int. Cl.
*C12N 15/113* (2010.01)
*A61K 31/713* (2006.01)
*A61P 13/12* (2006.01)

(52) U.S. Cl.
CPC .......... *C12N 15/113* (2013.01); *A61K 31/713* (2013.01); *A61P 13/12* (2018.01); *C12N 2310/14* (2013.01); *C12N 2310/315* (2013.01); *C12N 2310/321* (2013.01)

(58) Field of Classification Search
None
See application file for complete search history.

(56) References Cited

U.S. PATENT DOCUMENTS

2007/0082861 A1   4/2007 Matsuo
2015/0299704 A1*  10/2015 Duffield .................. A61P 13/00
514/44 A

FOREIGN PATENT DOCUMENTS

WO   2014/058881   4/2014

OTHER PUBLICATIONS

Yamamura et al. Nat Commun 11 2777, pp. 1-8 (Year: 2020).*
English translation of Nozu The Mother and Child Foundation, 26th Pediatric Research Report vol. 26, p. 16-17, pp. 1-7 (Year: 2015).*
Office Action dated Jun. 10, 2020 in corresponding Canadian Patent Application No. 3,047,894.
Nozu et al., "X-Linked Alport Syndrome Caused by Splicing Mutations in *COL4A5*", Clinical Journal of the American Society of Nephrology, 2014, vol. 9, pp. 1958-1964.
Watts et al., "Gene silencing by siRNAs and antisense oligonucleotides in the laboratory and the clinic", Journal of Pathology, 2012, vol. 226, No. 2, pp. 365-379.
International Search Report dated Mar. 20, 2018 in International Application No. PCT/JP2017/046304.
2015, vol. 26, p. 16-17, non-official translation (Nozu, Kandai et al., "Molecular therapeutic strategy using exon skipping therapy for alport syndrome", The Mother and Child Health Foundation: Research report for promoting pediatrics).
May 2017, vol. 30, No. 1, special issue, p. 102, (Japanese journal of pediatric nephrology), non-official translation (Shono, Akemi et al., "Alport syndrome-specific treatment method by exon skipping therapy").
International Preliminary Report on Patentability dated Jul. 11, 2019 in International (PCT) Application No. PCT/JP2017/046304, with English translation.
Extended European Search Report dated Nov. 18, 2020 in corresponding European Patent Application No. 17886231.4.
Yamamura et al., "Development of an exon skipping therapy for X-linked Alport syndrome with truncating variants in *COL4A5*", Nature Communications, 2020, vol. 11, No. 1, 8 pages.
Niks et at, "Exon skipping: a first in class strategy for Duchenne muscular dystrophy", Expert Opinion on Biological Therapy, 2016, vol. 17, No. 2, pp. 225-236.
Hashikami et al., "Establishment of X-linked Alport syndrome model mice with a *Col4a5* R471X mutation", Biochemistry and Biophysics Reports, vol. 17, 2019, pp. 81-86.

(Continued)

*Primary Examiner* — Brian Whiteman
(74) *Attorney, Agent, or Firm* — Wenderoth, Lind & Ponack, L.L.P.

(57) ABSTRACT

The present invention aims at establishing a molecular therapy for Alport syndrome. The present invention provides an oligonucleotide of 15-30 bp comprising a nucleotide sequence complementary to the cDNA of COL4A5 gene, wherein the oligonucleotide is capable of inducing skipping of an exon which has a truncating mutation found in COL4A5 gene in Alport syndrome patients and whose nucleotide number is a multiple of 3, a pharmaceutically acceptable salt thereof, or a solvate thereof. Also provided is a pharmaceutical drug comprising the above oligonucleotide, a pharmaceutically acceptable salt thereof, or a solvate thereof (therapeutic drug for Alport syndrome).

11 Claims, 18 Drawing Sheets
(13 of 18 Drawing Sheet(s) Filed in Color)
Specification includes a Sequence Listing.

(56) References Cited

OTHER PUBLICATIONS

Alves et al., "Clinical data and hearing of individuals with Alport syndrome", Brazilian Journal of Otorhinolaryngology, vol. 74, No. 6, 2008, pp. 807-814.

Koizumi, "Exon skipping therapeutic strategy using 2'-O,4'-C-ethylene-bridged nucleic acid (ENA®) oligonucleotides", AsiaTIDES meeting, Kyoto, Japan, Feb. 26. 2020, pp. 1-36.

\* cited by examiner

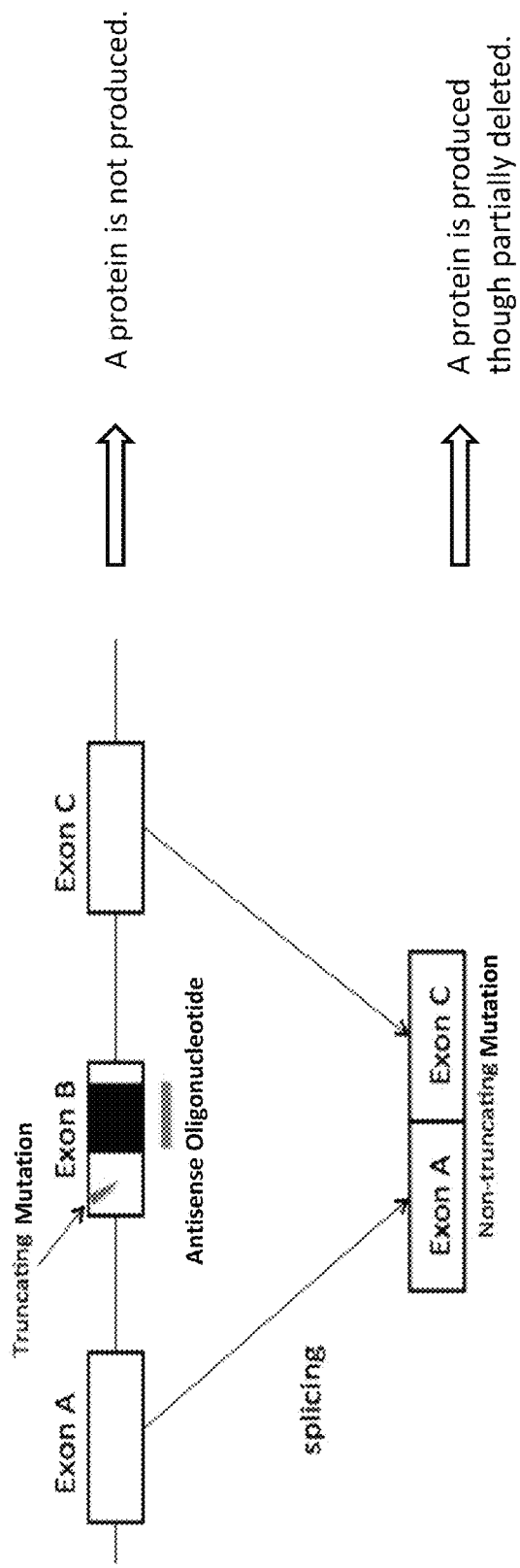

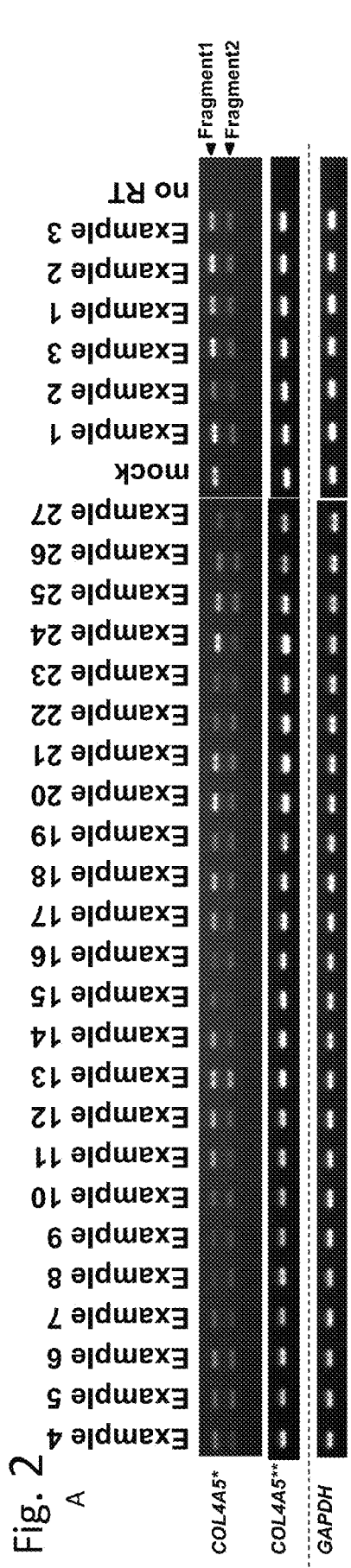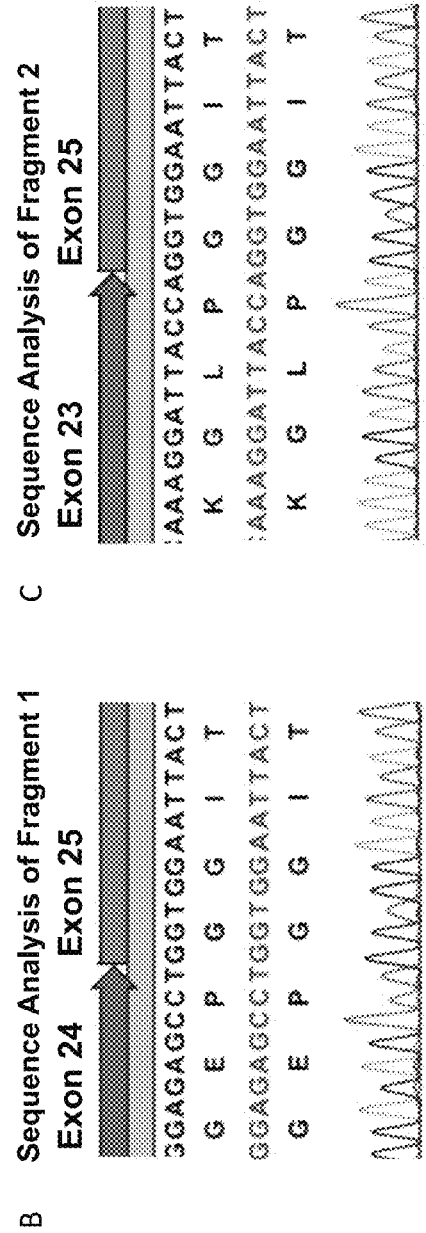

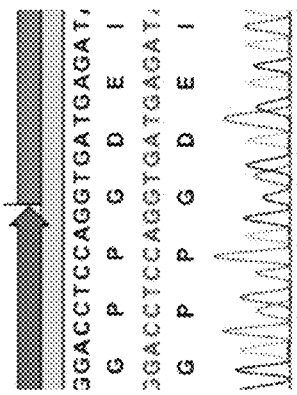
Fig. 5
A  COL4A5*  COL4A5**  GAPDH
* As primer for analysis, COL4A5 Exon 17-22 was used.
** As primer for analysis, COL4A5 Exon 1-7 was used.
B  Sequence Analysis of Fragment 3
C  Sequence Analysis of Fragment 4

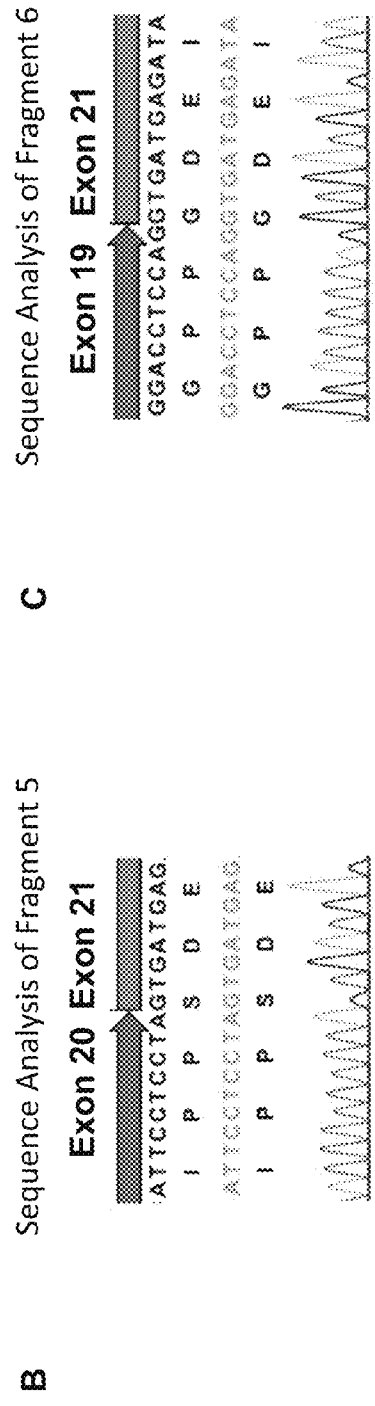
Fig. 7

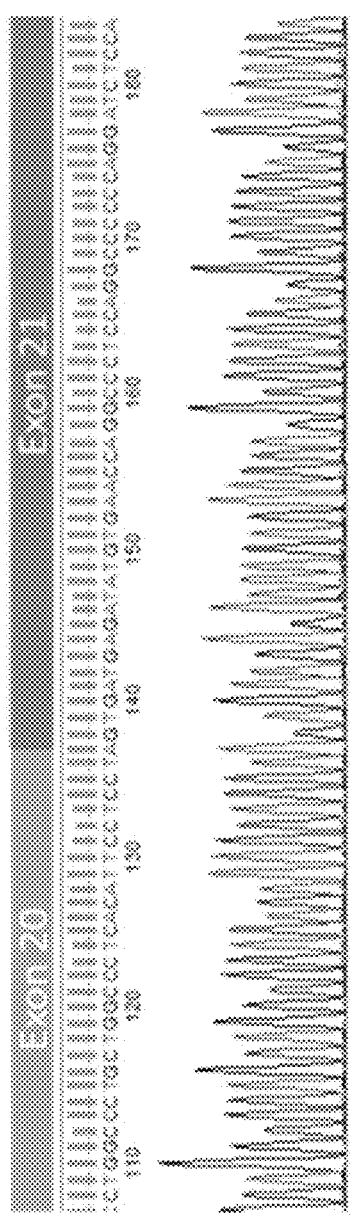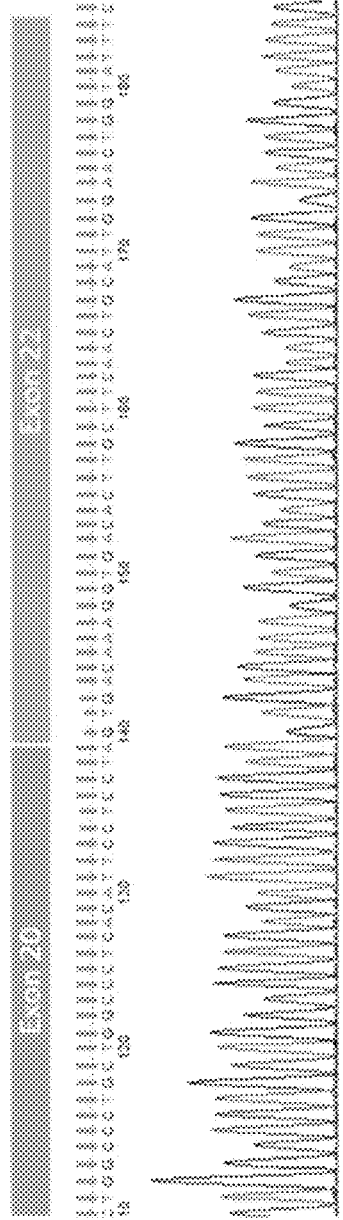
Fig. 13BC

Fig. 14
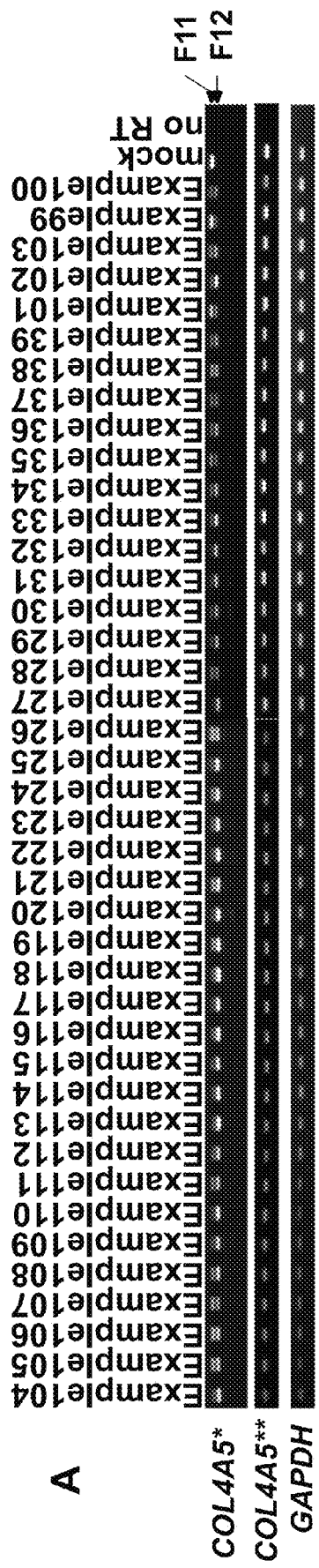
A
*As primer for analysis, COL4A5 Exon 18-24 was used.
**As primer for analysis, COL4A5 Exon 1-7 was used.
B: F11
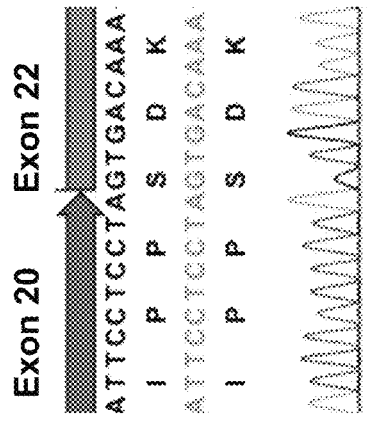
C: F12
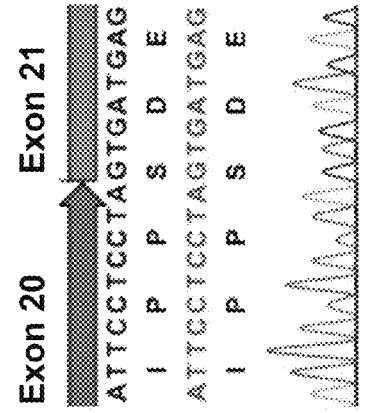

THERAPEUTIC DRUG FOR ALPORT'S SYNDROME

TECHNICAL FIELD

The present invention relates to a therapeutic for Alport syndrome. More specifically, the present invention relates to an oligonucleotide which is capable of inducing skipping of an exon having a truncating mutation found in COL4A5 gene in Alport syndrome patients and whose nucleotide number is a multiple of 3, as well as a pharmaceutical drug containing the oligonucleotide (preferably, a therapeutic for Alport syndrome).

BACKGROUND ART

Alport syndrome is a severe hereditary renal disease. In most cases, this disease progresses to end-stage renal disease (ESRD) by the age of 30 years. X-linked Alport syndrome (XLAS), the most common type of Alport syndrome, is caused by abnormalities in COL4A5 gene encoding type IV collagen α5 chain. The present inventors have so far conducted genetic diagnosis of XLAS patients from more than 300 families. The results revealed that, in about 15% of those families, patients have truncating mutations (such as nonsense mutation) which result in a failure to express proteins having complete chain lengths, and that these patients present clearly severer clinical pictures than patients having non-truncating mutations such as missense mutation (Non-Patent Document No. 1: Kidney Int. 2013, Vol. 85, pp. 1208-1213). Similar reports have also been made (Non-Patent Document No. 2: J Am Soc Nephrol. 2000, Vol. 11, pp. 649-657; Non-Patent Document No. 3: Nephrol Dial Transplant, 2002, Vol. 17, pp. 1218-1227; and Non-Patent Document No. 4: J Am Soc Nephrol, 2010, Vol. 21, pp. 876-883), and it has been found that the age of progression to ESRD is earlier by at least 10 years in patients with truncating mutations than in patients with non-truncating mutations.

PRIOR ART LITERATURE

Non-Patent Documents

Non-Patent Document No. 1: Kidney Int. 2013, Vol. 85, pp. 1208-1213
Non-Patent Document No. 2: J Am Soc Nephrol. 2000, Vol. 11, pp. 649-657
Non-Patent Document No. 3: Nephrol Dial Transplant, 2002, Vol. 17, pp. 1218-1227
Non-Patent Document No. 4: J Am Soc Nephrol, 2010, Vol. 21, pp. 876-883

DISCLOSURE OF THE INVENTION

Problem for Solution by the Invention

It is an object of the present invention to establish a molecular therapy for Alport syndrome.

Means to Solve the Problem

The present inventors have established a therapeutic method in which an antisense oligonucleotide (ASO) is administered to an Alport syndrome patient with truncating mutations to thereby induce skipping of exons having the truncating mutations (FIG. 1). In COL4A5 gene, 35 of its 44 exons constituting the collagenous domain are composed of nucleotides whose number is a multiple of 3. Therefore, by applying this therapeutic method to patients having truncating mutations in these 35 exons, the truncating mutations can be replaced with non-truncating mutations. Consequently, it becomes possible to delay the age of progression to ESRD in Alport syndrome patients presenting severe clinical pictures. The present study is the first developmental study of molecular therapy for XLAS in the world.

A summary of the present invention is as described below.

(1) An oligonucleotide of 15-30 bases comprising a nucleotide sequence complementary to the cDNA of COL4A5 gene, wherein the oligonucleotide is capable of inducing skipping of an exon which has a truncating mutation found in COL4A5 gene in Alport syndrome patients and whose nucleotide number is a multiple of 3, a pharmaceutically acceptable salt thereof, or a solvate thereof.

(2) The oligonucleotide of (1) above, which comprises a nucleotide sequence complementary to part of the nucleotide sequence of an exon which has a truncating mutation found in COL4A5 gene in Alport syndrome patients and whose nucleotide number is a multiple of 3, a pharmaceutically acceptable salt thereof, or a solvate thereof.

(3) The oligonucleotide of (1) or (2) above, wherein the exon which has a truncating mutation found in COL4A5 gene in Alport syndrome patients and whose nucleotide number is a multiple of 3 is exon 24, 20 or 21 of COL4A5 gene, a pharmaceutically acceptable salt thereof, or a solvate thereof.

(4) The oligonucleotide of any one of (1) to (3) above, comprising the whole or part of any of the sequences as shown in SEQ ID NOS: 1 to 28, 37 to 41, 51 and 52 (wherein "t" may be "u", and "u" may be "t"), a pharmaceutically acceptable salt thereof, or a solvate thereof.

(5) The oligonucleotide of any one of (1) to (4) above, wherein at least one of the sugar and/or the phosphodiester bond constituting the oligonucleotide is modified, a pharmaceutically acceptable salt thereof, or a solvate thereof.

(6) The oligonucleotide of (5) above, wherein the sugar constituting the oligonucleotide is D-ribofuranose and modification of the sugar is modification of the hydroxy group at 2'-position of D-ribofuranose, a pharmaceutically acceptable salt thereof, or a solvate thereof.

(7) The oligonucleotide of (6) above, wherein modification of the sugar is 2'-O-alkylation and/or 2'-O, 4'-C-alkylenation of D-ribofuranose, a pharmaceutically acceptable salt thereof, or a solvate thereof.

(8) The oligonucleotide of any one of (5) to (7) above, wherein modification of the phosphodiester bond is phosphorothioate bond, a pharmaceutically acceptable salt thereof, or a solvate thereof.

(9) A pharmaceutical drug comprising the oligonucleotide of any one of (1) to (8) above, a pharmaceutically acceptable salt thereof, or a solvate thereof

(10) A therapeutic drug for Alport syndrome, comprising the oligonucleotide of any one of (1) to (8) above, a pharmaceutically acceptable salt thereof, or a solvate thereof.

(11) A method of treating Alport syndrome, comprising administering to a subject a pharmaceutically effective amount of an oligonucleotide of 15-30 bases comprising a nucleotide sequence complementary to the cDNA of COL4A5 gene, the oligonucleotide being capable of inducing skipping of an exon which has a truncating mutation found in COL4A5 gene in Alport syndrome patients and whose nucleotide number is a multiple of 3, a pharmaceutically acceptable salt thereof, or a solvate thereof

(12) Use of an oligonucleotide of 15-30 bases comprising a nucleotide sequence complementary to the cDNA of COL4A5 gene, the oligonucleotide being capable of inducing skipping of an exon which has a truncating mutation found in COL4A5 gene in Alport syndrome patients and whose nucleotide number is a multiple of 3, a pharmaceutically acceptable salt thereof, or a solvate thereof, for treating Alport syndrome.

(13) An oligonucleotide of 15-30 bases comprising a nucleotide sequence complementary to the cDNA of COL4A5 gene, the oligonucleotide being capable of inducing skipping of an exon which has a truncating mutation found in COL4A5 gene in Alport syndrome patients and whose nucleotide number is a multiple of 3, a pharmaceutically acceptable salt thereof, or a solvate thereof, for use in a method of treating Alport syndrome.

Effect of the Invention

The present invention can be applied to patients having truncating mutations in exons of COL4A5 gene so that the truncating mutations are replaced with non-truncating mutations. As a result, it becomes possible to delay the age of progression to ESRD in Alport syndrome patients presenting severe clinical pictures. According to the present invention, it also becomes possible to prevent progress of hearing loss and ocular lesions.

The present specification encompasses the contents disclosed in the specifications and/or drawings of Japanese Patent Applications No. 2016-254906 and No. 2017-077374 based on which the present patent application claims priority.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 1 shows a schematic drawing explaining the principle of treatment with the therapeutic drug for Alport syndrome of the present invention.

FIG. 2 A part of the sequence of fragment 1 is shown in residues 3-23 of SEQ ID NO:53. A part of the sequence of fragment 2 is shown in SEQ ID NO:54. (A) A drawing showing the effects of compounds from Examples 1 to 27 on exon 24 of COL4A5. (B, C) Two drawings, with the left one showing the sequence of fragment 1 before the skipping of exon 24 takes place, and the right one showing the sequence of fragment 2 in which exon 24 has been skipped.

FIG. 5 A part of the sequence of fragment 3 is shown in SEQ ID NO:55. A part of the sequence of fragment 4 is shown in SEQ ID NO:56. (A) A drawing showing the effects of compounds from Examples 31 and 34 to 51 on exon 20 of COL4A5. (B, C) Two drawings, with the left one showing the sequence of fragment 3 before the skipping of exon 20 takes place, and the right one showing the sequence of fragment 4 in which exon 20 has been skipped.

FIG. 7 A part of the sequence of fragment 5 is shown in residues 1-18 of SEQ ID NO:55. A part of the sequence of fragment 6 is shown in SEQ ID NO:56. (A) A drawing showing the effects of compounds from Examples 31, 43 and 52 to 74 on exon 20 of COL4A5. (B, C) Two drawings, with the left one showing the sequence of fragment 5 before the skipping of exon 20 takes place, and the right one showing the sequence of fragment 6 in which exon 20 has been skipped.

FIG. 13BC (B, C) Two drawings, with the upper one showing the sequence of fragment 9 before the skipping of exon 21 takes place, and the lower one showing the sequence of fragment 10 in which exon 20 has been skipped.

FIG. 14 A part of the sequence of fragment 11 is shown in residues 1-18 of SEQ ID NO:55. A part of the sequence of fragment 12 is shown in SEQ ID NO:57. (A) A drawing showing the effects of compounds from Examples 99 to 139 on exon 21 of COL4A5. (B, C) Two drawings, with the left one showing the sequence of fragment 11 (indicated as "F11") before the skipping of exon 21 takes place, and the right one showing the sequence of fragment 12 (indicated as "F12") in which exon 21 has been skipped.

BEST MODES FOR CARRYING OUT THE INVENTION

Figure 3:
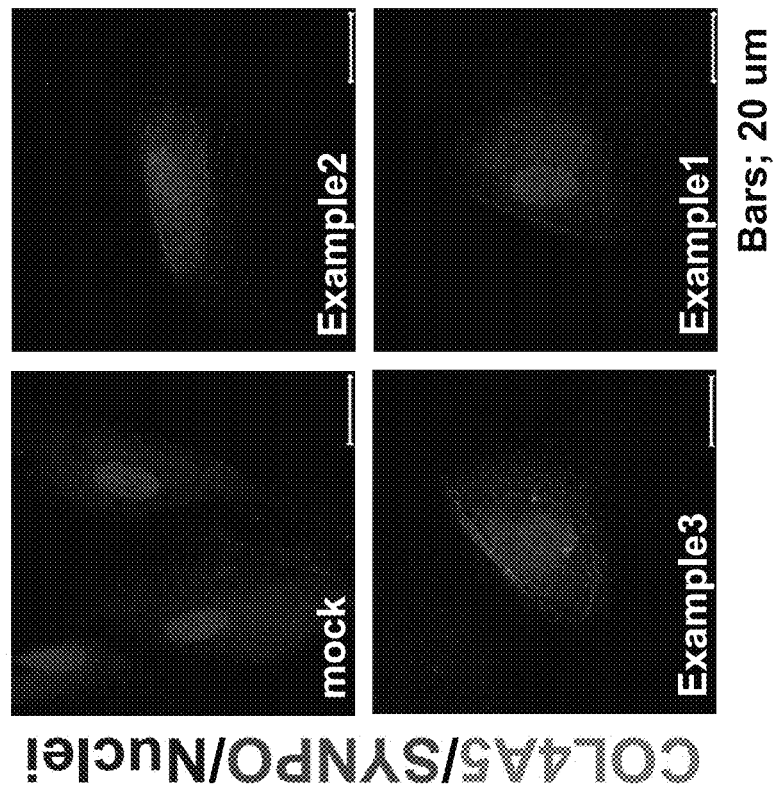
FIG. 3 Drawings showing increases in expressions of COL4A5 protein (green) and Synaptopodin (red) when oligonucleotides targeting exon 24 (from Examples 1 to 3) were introduced into renal glomerular epithelial cells (podocytes).

Hereinbelow, the present invention will be described in detail.

The present invention provides an oligonucleotide of 15-30 bases comprising a nucleotide sequence complementary to the cDNA of COL4A5 gene, wherein the oligonucleotide is capable of inducing skipping of an exon which has a truncating mutation found in COL4A5 gene in Alport syndrome patients and whose nucleotide number is a multiple of 3, a pharmaceutically acceptable salt thereof, or a solvate thereof.

In the present invention, Alport syndrome may be X-linked Alport syndrome (XLAS). XLAS is caused by mutations in COL4A5 gene encoding collagen IV α5 chain. In COL4A5 gene, 35 of its 44 exons constituting the collagenous domain are composed of nucleotides whose number is a multiple of 3. Therefore, if a patient has truncating mutations in these exons, replacement with non-truncating mutations is possible by a therapeutic method which comprises administering the oligonucleotide of the present invention to the patient.

A truncating mutation is a mutation in which protein synthesis is terminated prematurely as a result of a nonsense mutation, frameshift mutation, splice site mutation or the like. On the other hand, in a non-truncating mutation, protein synthesis is performed without shifting of the reading frame, though it has such a mutation as missense mutation, exon deletion mutation, etc.

Further, in an XLAS patient with a missense mutation who may potentially present a severer condition and who has the missense mutation located in an exon whose nucleotide number is a multiple of 3, exon skipping with the oligonucleotide of the present invention will produce a shortened protein but as long as it is functional, alleviation of XLAS is expected and the patient may be indicated for therapy with the oligonucleotide of the present invention.

Exons which are to be skipped by the oligonucleotide of the present invention may be exons whose nucleotide number is a multiple of 3 as selected from exons 3-46 located in the collagenous domain of COL4A5 gene. Exons whose nucleotide number is a multiple of 3 are exons 3-18, 20-22, 24, 26, 27, 30-35, 38-41 and 44-46.

The oligonucleotide of the present invention may be one that targets an exon which has a truncating mutation found in COL4A5 gene in Alport syndrome (in particular, XLAS) patients and whose nucleotide number is a multiple of 3. For example, the oligonucleotide of the present invention comprises a nucleotide sequence complementary to a sequence comprising 15 to 30 consecutive nucleotides in the nucleotide sequences of exons 3-18, 20-22, 24, 26, 27, 30-35, 38-41 and 44-46 in COL4A5 gene in Alport syndrome (in particular, XLAS) patients. Briefly, the oligonucleotide (antisense oligonucleotide) of the present invention may comprise a nucleotide sequence complementary to part of the nucleotide sequence of an exon which has a truncating mutation found in COL4A5 gene in Alport syndrome (in particular, XLAS) patients and whose nucleotide number is a multiple of 3 (e.g., exons 3-18, 20-22, 24, 26, 27, 30-35, 38-41 and 44-46)

As oligonucleotides that comprise a nucleotide sequence complementary to part of the nucleotide sequence of an exon which has a truncating mutation found in COL4A5 gene in Alport syndrome (in particular, XLAS) patients and whose nucleotide number is a multiple of 3, specific examples include, but are not limited to, oligonucleotides comprising the whole or part of any of the sequences as shown in SEQ ID NOS: 1 to 28, 37 to 41, 51 and 52 (wherein "t" may be "u", and "u" may be "t"). In the present invention, the expression "part of the sequence" usually means 80% or greater, preferably 85%, more preferably 90% and most preferably 94%, of the entire sequence of interest. The oligonucleotide of the present invention comprises nucleotides whose number is suitably 15-30, preferably 15-21, and more preferably 16-20.

Nucleotides constituting the oligonucleotide (antisense oligonucleotide) of the present invention may be either natural DNA, natural RNA, chimera DNA/RNA, or modified DNA, RNA or DNA/RNA. Preferably, at least one of the nucleotides is a modified nucleotide.

Examples of modified nucleotides include those in which sugar is modified (e.g., D-ribofuranose is 2'-O-alkylated or D-ribofuranose is 2'-O, 4'-C-alkylenated), those in which phosphodiester bond is modified (e.g., thioated), those in which base is modified, combinations of above-described nucleotides, and so forth. Antisense oligonucleotides in which at least one D-ribofuranose constituting the oligonucleotides is 2'-O-alkylated or 2'-O,4'-C-alkylenated have high RNA binding strength and high resistance to nuclease. Thus, they are expected to produce higher therapeutic effect than natural nucleotides (i.e. oligo DNA or oligo RNA). Further, oligonucleotides in which at least one phosphodiester bond constituting the oligonucleotides is thioated also have high resistance to nuclease and, thus, are expected to produce higher therapeutic effect than natural nucleotides (i.e. oligo DNA or oligo RNA). Oligonucleotides comprising both the modified sugar and the modified phosphate as described above have even higher resistance to nuclease and, thus, are expected to produce even higher therapeutic effect.

With respect to the oligonucleotide (anti sense oligonucleotide), examples of modified sugars include, but are not limited to, D-ribofuranose as 2'-O-alkylated (e.g. 2'-O-methylated, 2'-O-aminoethylated, 2'-O-propylated, 2'-O-allylated, 2'-O-methoxyethylated, 2'-O-butylated, 2'-O-pentylated, or 2'-O-propargylated); D-ribofuranose as 2'-O,4'-C-alkylenated (e.g. 2'-O,4'-C-ethylenated, 2'-O,4'-C-methylenated, 2'-O,4'-C-propylenated, 2'-O,4'-C-tetramethylated, or 2'-O,4'-C-pentamethylated); D-ribofuranose as 2'-deoxy-2'-C,4'-C-methyleneoxymethylated, S-cEt (2',4'-constrained ethyl), AmNA, 3'-deoxy-3'-amino-2'-deoxy-D-ribofuranose; and 3'-deoxy-3'-amino-2'-deoxy-2'-fluoro-D-ribofuranose.

With respect to the oligonucleotide (antisense oligonucleotide), examples of the modification of phosphodiester bond include, but are not limited to, phosphorothioate bond, methylphosphonate bond, methylthiophosphonate bond, phosphorodithioate bond and phosphoroamidate bond.

Examples of modified bases include, but are not limited to, cytosine as 5-methylated, 5-fluorinated, 5-brominated, 5-iodinated or N4-methylated; thymine as 5-demethylated (uracil), 5-fluorinated, 5-brominated or 5-iodinated; adenine as N6-methylated or 8-brominated; and guanine as N2-methylated or 8-brominated.

The oligonucleotide (antisense oligonucleotide) may be synthesized with a commercially available DNA synthesizer (e.g., PerkinElmer Model 392 based on the phosphoramidite method) according to the method described in Nucleic Acids Research, 12, 4539 (1984) with necessary modifications. As phosphoramidite reagents to be used in the process, natural nucleosides and 2'-O-methylnucleosides (i.e., 2'-O-methylguanosine, 2'-O-methyladenosine, 2'-O-methylcytidine and 2'-O-methyluridine) are commercially available. As regards 2'-O-alkylguanosine, -alkyladenosine, -alkylcytidine and -alkyluridine in which the carbon number of the alkyl group is 2-6, the following methods may be employed.

2'-O-aminoethylguanosine, -aminoethyladenosine, -aminoethylcytidine and -aminoethyluridine may be synthesized as previously described (Blommers et al., Biochemistry (1998), 37, 17714-17725).

2'-O-propylguanosine, -propyladenosine, -propylcytidine and -propyluridine may be synthesized as previously described (Lesnik, E. A. et al., Biochemistry (1993), 32, 7832-7838).

For the synthesis of 2'-O-allylguanosine, -allyladenosine, -allylcytidine and -allyluridine, commercially available reagents may be used.

2'-O-methoxyethylguanosine, -methoxyethyladenosine, -methoxyethylcytidine and -methoxyethyluridine may be synthesized as previously described (U.S. Pat. No. 6,261,840 or Martin, P. Helv. Chim. Acta. (1995) 78, 486-504).

2'-O-butylguanosine, -butyladenosine, -butylcytidine and -butyluridine may be synthesized as previously described (Lesnik, E. A. et al., Biochemistry (1993), 32, 7832-7838).

2'-O-pentylguanosine, -pentyladenosine, -pentylcytidine and -pentyluridine may be synthesized as previously described (Lesnik, E. A. et al., Biochemistry (1993), 32, 7832-7838).

For the synthesis of 2'-O-propargylguanosine, -propargyladenosine, -propargylcytidine and -propargyluridine, commercially available reagents may be used.

2'-O,4'-C-methyleneguanosine, 2'-O,4'-C-methyleneadenosine, 2'-O,4'-C-methylenecytidine, 5-methylcytidine and 5-methylthymidine may be prepared according to the method described in WO99/14226; and 2'-O,4'-C-alkyleneguanosine, 2'-O,4'-C-alkyleneadenosine, 2'-O,4'-C-methylenecytidine, 5-methylcytidine and 5-methylthymidine in which the carbon number of the alkylene group is 2-5 may be prepared according to the method described in WO00/47599.

Nucleosides in which D-ribofuranose is 2'-deoxy-2'-C,4'-C-methyleneoxymethylated may be synthesized as previously described (Wang, G. et al., Tetrahedron (1999), 55, 7707-774).

S-cEt (constrained ethyl) may be synthesized as previously described (Seth, P. P. et al. J. Org. Chem (2010), 75, 1569-1581).

AmNA may be synthesized as previously described (Yahara, A. et al. ChemBioChem (2012), 13, 2513-2516; or WO2014/109384).

Among nucleobases, uracil (U) and thymine (T) are interchangeable. Either uracil (U) or thymine (T) may be used for base pairing with adenine (A) in the complementary strand.

An antisense oligonucleotide with phophorothioate bonds can be synthesized by coupling phosphoramidite reagents and then reacting sulfur, tetraethylthiuram disulfide (TETD; Applied Biosystems), Beaucage reagent (Glen Research) or a reagent such as xanthan hydride (Tetrahedron Letters, 32, 3005 (1991); J. Am. Chem. Soc. 112, 1253 (1990); PCT/WO98/54198).

As controlled pore glass (CPG) to be used in a DNA synthesizer, 2'-O-methylnucleoside-bound CPG is commercially available. As regards 2'-O,4'-C-methyleneguanosine, 2'-O,4'-C-methyleneadenosine, 5-methyl cytidine and 5-methylthymidine, they may be prepared according to the method described in WO99/14226; and as regards 2'-O,4'-C-alkyleneguanosine, 2'-O,4'-C-alkyleneadenosine, 5-methylcytidine and 5-methylthymidine in which the carbon number of the alkylene group is 2-5, they may be prepared according to the method described in WO00/47599. The thus prepared nucleosides may then be bound to CPG as previously described (Oligonucleotide Synthesis, Edited by M. J. Gait, Oxford University Press, 1984). By using the modified CPG (as disclosed in Example 12b of Japanese Unexamined Patent Publication No. Hei7-87982), an oligonucleotide in which a 2-hydroxyethylphosphate group is bound at the 3' end can be synthesized. If 3'-amino-Modifier C3 CPG, 3'-amino-Modifier C7 CPG or Glyceryl CPG (Glen Research) or 3'-specer C3 SynBase CPG 1000 or 3'-specer C9 SynBase CPG 1000 (Link Technologies) is used, an oligonucleotide in which a hydroxyalkylphosphate group or aminoalkylphosphate group is bound at the 3' end can be synthesized.

The oligonucleotide (antisense oligonucleotide) of the present invention may be used for treating Alport syndrome.

The oligonucleotide (antisense oligonucleotide) may be used in the form of a pharmaceutically acceptable salt. The term "pharmaceutically acceptable salt" as used herein refers to salts of the oligonucleotide (antisense oligonucleotide). Examples of such salts include, but are not limited to, alkaline metal salts such as sodium salts, potassium salts or lithium salts; alkaline earth metal salts such as calcium salts or magnesium salts; metal salts such as aluminum salts, iron salts, zinc salts, copper salts, nickel salts or cobalt salts; amine salts including inorganic salts such as ammonium salts and organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts or tris(hydroxymethyl)aminomethane salts; inorganic acid salts including hydrohalogenic acid salts such as hydrofluorides, hydrochlorides, hydrobromides or hydroiodides, as well as nitrates, perchlorates, sulfates or phosphates; organic acid salts including lower alkane sulfonic acid salts such as methanesulfonates, trifluoromethanesulfonates or ethanesulfonates, arylsulfonic acid salts such as benzenesulfonates or p-toluenesulfonates, as well as acetates, malates, fumarates, succinates, citrates, tartrates, oxalates or maleates; and amino acid salts such as glycine salts, lysine salts, arginine salts, ornithine salts, glutamic acid salts or aspartic acid salts. These salts may be prepared by known methods.

The oligonucleotide (antisense oligonucleotide) or a pharmaceutically acceptable salt thereof sometimes occur as a solvate (e.g., hydrate). The oligonucleotide (antisense oligonucleotide) or a pharmaceutically acceptable salt thereof of the present invention may be such a solvate.

When the oligonucleotide (antisense oligonucleotide) of the present invention, a pharmaceutically acceptable salt thereof or a solvate thereof is used for treatment of Alport syndrome, they may be administered per se or mixed with appropriate, pharmaceutically acceptable excipients, diluents, and the like for oral administration in the form of tablets, capsules, granules, powders, syrups, etc. or for parenteral administration in the form of injections, suppositories, patches or external preparations.

These formulations may be prepared by well-known methods using additives such as excipients (e.g., organic excipients including sugar derivatives such as lactose, sucrose, glucose, mannitol or sorbitol; starch derivatives such as corn starch, potato starch, α-starch or dextrin; cellulose derivatives such as crystalline cellulose; gum arabic; dextran; or pullulan; and inorganic excipients including silicate derivatives such as light anhydrous silicic acid, synthetic aluminum silicate, calcium silicate or magnesium aluminometasilicate; phosphates such as calcium hydrogenphosphate; carbonates such as calcium carbonate; and sulfates such as calcium sulfate), lubricants (e.g., stearic acid; metal salts of stearic acid such as calcium stearate and magnesium stearate; talc; colloidal silica; waxes such as beeswax and spermaceti; boric acid; adipic acid; sulfates such as sodium sulfate; glycol; fumaric acid; sodium benzoate; DL-leucine; lauryl sulfates such as sodium lauryl sulfate or magnesium lauryl sulfate; silicic acid compounds such as silicic anhydride and silicic hydrate; or the starch derivatives listed above), binders (e.g., hydroxypropylcellulose, hydroxypropylmethylcellulose, polyvinylpyrrolidone, macrogol, or compounds similar to the above-listed excipients), disintegrants (e.g., cellulose derivatives such as low-substituted hydroxypropylcellulose, carboxymethylcellulose, calcium carboxymethylcellulose or internally crosslinked sodium carboxymethylcellulose; and chemically modified starch/cellulose derivatives such as carboxymethylstarch, sodium carboxymethylstarch or crosslinked polyvinylpyrrolidone), emulsifiers (e.g., colloidal clay such as bentonite or veegum; metal hydroxides such as magnesium hydroxide or aluminum hydroxide; anionic surfactants such as sodium lauryl sulfate or calcium stearate; cationic surfactants such as benzalkonium chloride; or nonionic surfactants such as polyoxyethylenealkylether, polyoxyethylene sorbitan fatty acid ester or sucrose esters of fatty acids), stabilizers (e.g., p-hydroxybenzoate esters such as methylparaben or propylparaben; alcohols such as chlorobutanol, benzyl alcohol or phenylethyl alcohol; benzalkonium chloride; phenols such as phenol or cresol; thimerosal; dehydroacetic acid; or sorbic acid), flavoring agents (e.g., conventionally used sweeteners, acidifiers, flavors and the like) or diluents.

The therapeutic drug of the present invention may comprise 0.1-250 µmoles/ml, preferably 1-50 µmole/ml of oligonucleotide (antisense oligonucleotide), pharmaceutically acceptable salt thereof or solvate thereof; 0.02-10% w/v of carbohydrate or polyalcohol; and 0.01-0.4% w/v of pharmaceutically acceptable surfactant.

As the above carbohydrate, monosaccharides and/or disaccharides are especially preferable. Specific examples of these carbohydrates and polyalcohols include, but are not limited to, glucose, galactose, mannose, lactose, maltose, mannitol and sorbitol. These may be used alone or in combination.

Preferable examples of the surfactant include, but are not limited to, polyoxyethylene sorbitan mono-, di- or tri-ester, alkylphenylpolyoxyethylene, sodium taurocholate, sodium cholate and polyalcohol esters. Among these, polyoxyethylene sorbitan mono-, di- and tri-ester are especially preferable; the most preferable esters are oleate, laurate, stearate and palmitate. These may be used alone or in combination.

More preferably, the therapeutic drug of the present invention may comprise 0.03-0.09 M pharmaceutically acceptable neutral salt such as sodium chloride, potassium chloride and/or calcium chloride.

Even more preferably, the therapeutic drug of the present invention may comprise 0.002-0.05 M pharmaceutically acceptable buffer. Examples of a preferable buffer include, but are not limited to, sodium citrate, sodium glycinate, sodium phosphate and tris(hydroxymethyl)aminomethane. These buffers may be used alone or in combination.

Further, the above-described drug may be supplied in a state of solution. However, as in the case where there is a need for storage over a certain period of time, the drug is preferably lyophilized for stabilizing the oligonucleotide (antisense oligonucleotide) to thereby prevent the lowering of its therapeutic effect. When lyophilized, the drug may be reconstructed with a solution, such as distilled water for injection, just before use. Thus, the drug is returned into the state of a liquid to be administered. Therefore, the therapeutic drug of the present invention encompasses one in a lyophilized state that is used after reconstruction with a solution so that the respective components fall within specified concentration ranges. For the purpose of promoting the solubility of the lyophilized product, the drug may further comprise albumin and amino acids such as glycine.

When the oligonucleotide (antisense oligonucleotide) of the invention, a pharmaceutically acceptable salt thereof or a solvate thereof is administered to a human, the oligonucleotide or the like may be administered, for example, at approximately 0.01-100 mg/kg (body weight), preferably at 0.1-20 mg/kg (body weight) per adult per day either once or over several times by subcutaneous injection, intravenous infusion or intravenous injection. The dose and the number of times of administration may be changed appropriately depending on the type and symptoms of the disease, the age of the patient, administration route, etc.

Administration of the oligonucleotide (antisense oligonucleotide) of the invention, a pharmaceutically acceptable salt thereof or a solvate thereof to Alport syndrome patients may be performed, for example, as described below. Briefly, the antisense oligonucleotide, pharmaceutically acceptable salt thereof or solvate thereof is prepared by methods well-known to one of ordinary skill in the art and sterilized by conventional methods to prepare, for example, 125 mg/ml of an injection solution. This solution is instilled to a patient intravenously in the form of, for example, infusion so that the dose of the oligonucleotide (antisense oligonucleotide) is, for example, 10 mg per kg body weight. This administration is repeated, for example, at 1-week intervals. Subsequently, this treatment is appropriately repeated while confirming the therapeutic effect by examining reduction of urine protein, inhibition of progression of renal dysfunction, etc.

The therapeutic drug for Alport syndrome of the present invention may be used jointly with other therapeutic drugs such as ACE inhibitors or angiotensin receptor antagonists.

EXAMPLES

Hereinbelow, the present invention will be described more specifically with reference to the following Examples. These Examples are given only for explanation and are not intended to limit the scope of the present invention.

Example 1

(SEQ ID NO: 1)
$HO-C^{mls}-C^{e2s}-C^{mls}-U^{mls}-G^{e2s}-G^{mls}-C^{mls}-A^{e2s}-A^{mls}-U^{mls}-C^{e2s}-C^{mls}-A^{mls}-T^{e2s}-C^{mls}-C^{mls}-T^{e2s}-G^{mlr}-H$ (ex24_011)

Synthesis was performed with an automated nucleic acid synthesizer (BioAutomation's MerMade 192X) by the phosphoramidite method (Nucleic Acids Research, 12, 4539 (1984)). As reagents, Activator Solution-3 (0.25 mol/L 5-Benzylthio-1H-tetrazole-Acetonitrile Solution; Wako Pure Chemical; product No. 013-20011), Cap A for AKTA (1-Methylimidazole-Acetonitrile Solution; Sigma-Aldrich; product No. L040050), Cap B1 for AKTA (Acetic Anhydride, Acetonitrile Solution; Sigma-Aldrich; product No. L050050), Cap B2 for AKTA (Pyridine-Acetonitrile Solution; Sigma-Aldrich; product No. L050150), and DCA Deblock (Dichloroacetic Acid-Toluene Solution; Sigma-Aldrich; product No. L023050) were used. As a thioation reagent for formation of phosphorothioate bond, phenylacetyl disulfide (Carbosynth; product No. FP07495) was dissolved in a 1:1 (v/v) solution of acetonitrile (dehydrated;

Kanto Chemical Co., Inc.; product No. 01837-05) and pyridine (dehydrated; Kanto Chemical Co., Inc.; product No. 11339-05) to give a concentration of 0.2 M. As amidite reagents, 2'-O-Me nucleoside phosphoramidites (for adenosine: product No. ANP-5751; for cytidine: product No. ANP-5752; for guanosine: product No. ANP-5753; for uridine: product No. ANP-5754) were products from ChemGenes. Non-natural phosphoramidites used were the following compounds disclosed in the indicated Examples of Japanese Unexamined Patent Publication No. 2000-297097: Example 14 (5'-O-dimethoxytrityl-2'-O,4'-C-ethylene-6-N-benzoyladenosine-3'-O-(2-cyanoethyl N,N-diisopropyl)phosphoramidite); Example 27 (5'-O-dimethoxytrityl-2'-O,4'-C-ethylene-2-N-isobutylguanosine-3'-O-(2-cyanoethyl N,N-diisopropyl)phosphoramidite); Example 22 (5'-O-dimethoxytrityl-2'-O,4'-C-ethylene-4-N-benzoyl-5-methylcytidine-3'-O-(2-cyanoethyl N,N-diisopropyl)phosphoramidite); and Example 9 (5'-O-dimethoxytrityl-2'-O,4'-C-ethylene-5-methyluridine-3'-O-(2-cyanoethyl N,N-diisopropyl)phosphoramidite). As a solid carrier, Glen Unysupport™ FC 96 well format 0.2 µmol (GlenResearch) was used. Thus, the subject compound was synthesized. It should be noted here that about 9 minutes was set as the time required for condensation of amidites.

Protected oligonucleotide analogs with the sequence of interest were treated with 600 µl of thick aqueous ammonia to thereby cut out oligomers from the support and, at the same time, remove the protective group cyanoethyl on phosphorus atoms and the protective group on nucleobases. The resultant oligomer mixture in solution was mixed with 300 µl of Clarity QSP DNA Loading Buffer (Phenomenex) and charged on Clarity SPE 96 well plates (Phenomenex). One milliliter of Clarity QSP DNA Loading Buffer:water=1:1 solution, 3 mL of water, 3 ml of 3% dichloroacetic acid (DCA) aqueous solution and 6 ml of water were added in this order. Subsequently, components extracted with a 9:1 solution of 20 mM Tris aqueous solution and acetonitrile were collected. After distilling off the solvent, the compound of interest was obtained. When analyzed by reversed-phase HPLC [column (Phenomenex, Clarity 2.6 µm Oligo-MS 100A (2.1×50 mm)), Solution A: an aqueous solution of 100 mM hexafluoroisopropanol (HFIP) and 8 mM trimethylamine, Solution B: methanol, B %: from 10% to 25% (4 min, linear gradient); 60° C.; 0.5 mL/min; 260 nm)], the subject compound was eluted at 2.887 min. The compound was identified by negative-ion ESI mass spectrometry (theoretical: 6276.73; found: 6276.64)

The nucleotide sequence of the subject compound is a sequence complementary to nucleotide Nos. 162604 to 162621 of *Homo sapiens* collagen type IV alpha 5 chain (COL4A5) (NCBI-GenBank accession No. NG_011977).

Compounds of Examples 2 and 3 were also synthesized in the same manner as described in Example 1. Data from Examples 1 to 3 are summarized in Table 1 below.

In sequences shown in the Table, capital letters represent ENA and small letters 2'-OMe-RNA. For "Start" and "End", respective nucleotide numbers in *Homo sapiens* collagen type IV alpha 5 chain (COL4A5) (NCBI-GenBank accession No. NG_011977) are shown. Molecular weights in the Table show values as measured by negative-ion ESI mass spectrometry.

Example 4

$$\text{(SEQ ID NO: 1)}$$
$$\text{HO-}C^{m1s}\text{-}C^{e2s}\text{-}C^{m1s}\text{-}T^{e2s}\text{-}G^{m1s}\text{-}G^{m1s}\text{-}C^{e2s}\text{-}A^{m1s}\text{-}A^{m1s}\text{-}U^{m1s}\text{-}C^{m1s}\text{-}$$
$$C^{e2s}\text{-}A^{m1s}\text{-}U^{m1s}\text{-}C^{e2s}\text{-}C^{m1s}\text{-}T^{e2s}\text{-}G^{m1r}\text{-H}(\text{ex24\_c01})$$

Protected oligonucleotide analogs with the sequence of interest synthesized under the same conditions as described in Example 1 were treated with 600 µl of thick aqueous ammonia to thereby cut out oligomers from the support and, at the same time, remove the protective group cyanoethyl on phosphorus atoms and the protective group on nucleobases. The resultant oligomer mixture in solution was mixed with 300 µl of Clarity QSP DNA Loading Buffer (Phenomenex) and charged on Clarity SPE 96 well plates (Phenomenex). One milliliter of a 1:1 solution of Clarity QSP DNA Loading Buffer and water, 1 mL of a 8:2 solution of 0.1 M triethylammonium hydrogencarbonate aqueous solution (TEAB) and water, 3 ml of 3% dichloroacetic acid (DCA) aqueous solution, 2 ml of water and 1 ml of 20 mM Tris aqueous solution were added in this order. Subsequently, components extracted with a 9:1 solution of 20 mM Tris aqueous solution and acetonitrile were collected. After distilling off the solvent, the compound of interest was obtained. When analyzed by reversed-phase HPLC [column (Phenomenex, Clarity 2.6 µm Oligo-MS 100A (2.1×50 mm)), Solution A: an aqueous solution of 100 mM hexafluoroisopropanol (HFIP) and 8 mM trimethylamine, Solution B: methanol, B %: from 10% to 25% (4 min, linear gradient); 60° C.; 0.5 mL/min; 260 nm)], the subject compound was eluted at 2.733 min. The compound was identified by negative-ion ESI mass spectrometry (thoretical: 6304.76; found: 6304.75).

The nucleotide sequence of the subject compound is a sequence complementary to nucleotide Nos. 162604 to 162621 of *Homo sapiens* collagen type IV alpha 5 chain (COL4A5) (NCBI-GenBank accession No. NG_011977).

Compounds of Examples 5 to 27 were also synthesized in the same manner as described in Example 4. Data from Example 4 and Examples 5 to 27 are summarized in Table 2 below.

TABLE 1

| Example | Designation | Sequence (5'-3') | Start | End | Molecular Weight | SEQ ID NO: |
|---|---|---|---|---|---|---|
| 1 | ex24_011 | cCcuGgcAauCcaTccTg | 162604 | 162621 | 6276.64 | 1 |
| 2 | ex24_b04 | cCugGcaAucCauCcuGu | 162603 | 162620 | 6263.60 | 2 |
| 3 | ex24_b05 | cTggCaaTccAucCugTc | 162602 | 162619 | 6291.66 | 3 |

TABLE 2

| Example | Designation | Sequence (5'-3') | Start | End | Molecular Weight | SEQ ID NO: |
|---|---|---|---|---|---|---|
| 4 | ex24_c01 | cCcTggCaaucCauCcTg | 162604 | 162621 | 6304.75 | 1 |
| 5 | ex24_c02 | cCcTggCaaucCauCCTg | 162604 | 162621 | 6304.74 | 1 |
| 6 | ex24_c03 | cCcTggCaaTcCauCcTg | 162604 | 162621 | 6330.76 | 1 |
| 7 | ex24_c04 | CcCuggCaaTcCauCcTg | 162604 | 162621 | 6330.76 | 1 |
| 8 | ex24_c05 | cCcTggCaAuCcAuCcTg | 162604 | 162621 | 6328.75 | 1 |
| 9 | ex24_c06 | cCcTggCaaTcCaTcCTg | 162604 | 162621 | 6356.79 | 1 |
| 10 | ex24_c07 | CCcTggCaaTcCaTcCTg | 162604 | 162621 | 6382.80 | 1 |
| 11 | ex24_c08 | cCcTgGcAaTcCaTcCuG | 162604 | 162621 | 6340.74 | 1 |
| 12 | ex24_c09 | cCuggCaaTcCauCcTgu | 162603 | 162620 | 6305.74 | 2 |
| 13 | ex24_c10 | CcTggCaauccauCcTgT | 162603 | 162620 | 6305.74 | 2 |
| 14 | ex24_c11 | cCuggCaaTcCauCcTgT | 162603 | 162620 | 6661.74 | 2 |
| 15 | ex24_c12 | ccTggCaAuCcAuCcTgu | 162603 | 162620 | 6303.72 | 2 |
| 16 | ex24_c13 | cCTggCaaTcCauCcTgT | 162603 | 162620 | 6357.76 | 2 |
| 17 | ex24_c14 | CcTggCaAuCcAuCcTgu | 162603 | 162620 | 6329.73 | 2 |
| 18 | ex24_c15 | cCTggCaaTcCaTCcTgT | 162603 | 162620 | 6383.78 | 2 |
| 19 | ex24_c16 | CcTggCaAuCcAuCcTgT | 162603 | 162620 | 6355.75 | 2 |
| 20 | ex24_c17 | cTggCaaTccaTcCugTc | 162602 | 162619 | 6305.73 | 3 |
| 21 | ex24_c18 | cTggCaauCcaTccTguC | 162602 | 162619 | 6305.73 | 3 |
| 22 | ex24_c19 | cTggCaaTcCaTcCugTc | 162602 | 162619 | 6331.77 | 3 |
| 23 | ex24_c20 | CTggCaauCcaTcCugTc | 162602 | 162619 | 6331.75 | 3 |
| 24 | ex24_c21 | cTggCaAuCcAuCcTgTc | 162602 | 162619 | 6329.74 | 3 |
| 25 | ex24_c22 | CTggCaaTccAucCugTC | 162602 | 162619 | 6343.75 | 3 |
| 26 | ex24_c23 | CTggCaaTcCaTcCugTC | 162602 | 162619 | 6383.78 | 3 |
| 27 | ex24_c24 | cTgGcAaTcCaTcCuGuC | 162602 | 162619 | 6341.74 | 3 |

In sequences shown in the Table, capital letters represent ENA and small letters 2'-OMe-RNA. For "Start" and "End", respective nucleotide numbers in *Homo sapiens* collagen type IV alpha 5 chain (COL4A5) (NCBI-GenBank accession No. NG_011977) are shown. Molecular weights in the Table show values as measured by negative-ion ESI mass spectrometry.

Example 28

(SEQ ID NO: 4)
HO-U$^{m1s}$-A$^{e2s}$-U$^{m1s}$-A$^{m1s}$-G$^{e2s}$-C$^{m1s}$-U$^{m1s}$-T$^{e2s}$-A$^{m1s}$-C$^{m1s}$-T$^{e2s}$-A$^{m1s}$-G$^{m1s}$-G$^{e2s}$-A$^{m1s}$-G$^{m1s}$-G$^{e2s}$-A$^{m1t}$-H (ex20_001)

The compound of interest was obtained by performing synthesis and purification under the same conditions as described in Example 1. When analyzed by reversed-phase HPLC [column (Phenomenex, Clarity 2.6 µm Oligo-MS 100A (2.1×50 mm)), Solution A: an aqueous solution of 100 mM hexafluoroisopropanol (HFIP) and 8 mM trimethylamine, Solution B: methanol, B %: from 10% to 25% (4 min, linear gradient); 60° C.; 0.5 mL/min; 260 nm)], the subject compound was eluted at 3.113 min. The compound was identified by negative-ion ESI mass spectrometry (theoretical: 6401.73; found: 6401.69).

The nucleotide sequence of the subject compound is a sequence complementary to nucleotide Nos. 156301 to 156318 of *Homo sapiens* collagen type IV alpha 5 chain (COL4A5) (NCBI-GenBank accession No. NG_011977).

The compounds of Examples 29 to 33 were also synthesized in the same manner as described in Example 28. Data from Example 28 and from Examples 29 to 33 are summarized in Table 3 below.

TABLE 3

| Example | Designation | Sequence (5'-3') | Start | End | Molecular Weight | SEQ ID NO: |
|---|---|---|---|---|---|---|
| 28 | ex20_001 | uAuaGcuTacTagGagGa | 156301 | 156318 | 6401.69 | 4 |
| 29 | ex20_002 | gCuuAcuAggAggAauGu | 156297 | 156314 | 6403.65 | 5 |
| 30 | ex20_022 | gGagGucCagGaaTggAa | 156217 | 156234 | 6518.74 | 6 |
| 31 | ex20_023 | gTccAggAauGgaAauTc | 156213 | 156230 | 6400.68 | 7 |
| 32 | ex20_024 | aGgaAugGaaAuuCcaGg | 156209 | 156226 | 6449.71 | 8 |
| 33 | ex20_044 | uAacTgcAgcCccTaaGa | 156129 | 156146 | 6333.72 | 9 |

In sequences shown in the Table, capital letters represent ENA and small letters 2'-OMe-RNA. For "Start" and "End", respective nucleotide numbers in *Homo sapiens* collagen type IV alpha 5 chain (COL4A5) (NCBI-GenBank accession No. NG_011977) are shown. Molecular weights in the Table show values as measured by negative-ion ESI mass spectrometry.

Examples 34-74

$$\text{HO-}A^{m1s}\text{-}A^{e2s}*U^{m1s}\text{-}A^{m1s}\text{-}T^{e2s}\text{-}A^{m1s}\text{-}G^{m1s}\text{-}C^{e2s}\text{-}U^{m1s}\text{-}U^{m1s}\text{-}A^{e2s}\text{-}C^{m1s}\text{-}U^{m1s}\text{-}A^{e2s}\text{-}G^{m1s}\text{-}G^{m1s}\text{-}A^{e2s}\text{-}G^{m1r}\text{-H (ex20\_b02)}$$
(SEQ ID NO: 10)

The compound of interest was obtained by performing synthesis and purification under the same conditions as described in Example 4. When analyzed by reversed-phase HPLC [column (Phenomenex, Clarity 2.6 μm Oligo-MS 100A (2.1×50 mm)), Solution A: an aqueous solution of 100 mM hexafluoroisopropanol (HFIP) and 8 mM trimethylamine, Solution B: methanol, B %: from 10% to 25% (4 min, linear gradient); 60° C.; 0.5 mL/min; 260 nm)], the subject compound was eluted at 3.213 min. The compound was identified by negative-ion ESI mass spectrometry (theoretical: 6385.74; found: 6385.78).

The nucleotide sequence of the subject compound is a sequence complementary to nucleotide Nos. 156303 to 156320 of *Homo sapiens* collagen type IV alpha 5 chain (COL4A5) (NCBI-GenBank accession No. NG_011977).

The compounds of Examples 35 to 74 were also synthesized in the same manner as described in Example 34. Data from Example 34 and from Examples 35 to 74 are summarized in Table 4 below.

TABLE 4

| Example | Designation | Sequence (5'-3') | Start | End | Molecular Weight | SEQ ID NO: |
|---|---|---|---|---|---|---|
| 34 | ex20_b02 | aAuaTagCuuAcuAggAg | 156303 | 156320 | 6385.78 | 10 |
| 35 | ex20_b03 | aTauAgcTuaCuaGgaGg | 156302 | 156319 | 6415.82 | 11 |
| 36 | ex20_b04 | aTagCuuAcuAggAggAa | 156300 | 156317 | 6424.80 | 12 |
| 37 | ex20_b05 | uAgcTuaCuaGgaGgaAu | 156299 | 156316 | 6401.77 | 13 |
| 38 | ex20_b07 | cTuaCuaGgaGgaAugTg | 156296 | 156313 | 6431.74 | 14 |
| 39 | ex20_b09 | uAcuAggAggAauGugAg | 156294 | 156311 | 6452.71 | 15 |
| 40 | ex20_b10 | gAggTccAggAauGgaAa | 156216 | 156233 | 6488.77 | 16 |
| 41 | ex20_b11 | aGguCcaGgaAugGaaAu | 156215 | 156232 | 6449.75 | 17 |
| 42 | ex20_b12 | gGucCagGaaTggAaaTu | 156214 | 156231 | 6454.75 | 18 |
| 43 | ex20_b13 | uCcaGgaAugGaaAuuCc | 156212 | 156229 | 6360.71 | 19 |
| 44 | ex20_b14 | cCagGaaTggAaaTucCa | 156211 | 156228 | 6411.78 | 20 |
| 45 | ex20_b15 | cAggAauGgaAauTccAg | 156210 | 156227 | 6409.73 | 21 |
| 46 | ex20_b16 | cCauAacTgcAgcCccTa | 156132 | 156149 | 6283.74 | 22 |
| 47 | ex20_b17 | cAuaAcuGcaGccCcuAa | 156131 | 156148 | 6283.74 | 23 |
| 48 | ex20_b18 | aTaaCugCagCccCuaAg | 156130 | 156147 | 6361.79 | 24 |
| 49 | ex20_b19 | aAcuGcaGccCcuAagAu | 156128 | 156145 | 6305.72 | 25 |

TABLE 4-continued

| Example | Designation | Sequence (5'-3') | Start | End | Molecular Weight | SEQ ID NO: |
|---|---|---|---|---|---|---|
| 50 | ex20_b20 | aCugCagCccCuaAgaTu | 156127 | 156144 | 6338.76 | 26 |
| 51 | ex20_b21 | cTgcAgcCccTaaGauTc | 156126 | 156143 | 6300.73 | 27 |
| 52 | ex20_c01 | gTcCaggAaTggaaAuTc | 156213 | 156230 | 6428.77 | 28 |
| 53 | ex20_c02 | gTcCaggAaTggaaaTuC | 156213 | 156230 | 6442.78 | 28 |
| 54 | ex20_c03 | gTCcaggaATggaaaTTc | 156213 | 156230 | 6442.78 | 28 |
| 55 | ex20_c04 | gTccAggAaTggaAauTc | 156213 | 156230 | 6414.75 | 28 |
| 56 | ex20_c05 | gTccAggAauggaAauTc | 156213 | 156230 | 6388.73 | 28 |
| 57 | ex20_c06 | gTcCaggaaTggaaaTuC | 156213 | 156230 | 6430.78 | 28 |
| 58 | ex20_c07 | gTcCaggaaTggaaAuTc | 156213 | 156230 | 6416.77 | 28 |
| 59 | ex20_c08 | gTccAggaaTggAaaTuc | 156213 | 156230 | 6402.76 | 28 |
| 60 | ex20_c09 | gTccAggaauggaAauTc | 156213 | 156230 | 6376.73 | 28 |
| 61 | ex20_c10 | gTcCaggaauggaaaTuC | 156213 | 156230 | 6404.76 | 28 |
| 62 | ex20_c11 | gTcCaggaaTggaaauTc | 156213 | 156230 | 6404.77 | 28 |
| 63 | ex20_c12 | uCcAggAaTggAaAuuCc | 156212 | 156229 | 6386.75 | 19 |
| 64 | ex20_c13 | TccAggAauggAaaTucC | 156212 | 156229 | 6374.74 | 19 |
| 65 | ex20_c14 | uCcAggaAuggAaAuuCc | 156212 | 156229 | 6360.73 | 19 |
| 66 | ex20_c15 | TcCaggAaTggaaaTuCc | 156212 | 156229 | 6402.77 | 19 |
| 67 | ex20_c16 | uCcAggAaTggaaaTuCc | 156212 | 156229 | 6388.77 | 19 |
| 68 | ex20_c17 | uCcAggAaTggaaaTuCc | 156212 | 156229 | 6360.73 | 19 |
| 69 | ex20_c18 | uCcAggaauggaAaTuCc | 156212 | 156229 | 6362.74 | 19 |
| 70 | ex20_c19 | TcCaggaaTggaaaTuCc | 156212 | 156229 | 6390.77 | 19 |
| 71 | ex20_c20 | TcCaggaaTggaaauTcC | 156212 | 156229 | 6390.77 | 19 |
| 72 | ex20_c21 | uCcAggaauggaaaTuCc | 156212 | 156229 | 6350.74 | 19 |
| 73 | ex20_c22 | uCcaggAauggAaauuCc | 156212 | 156229 | 6336.73 | 19 |
| 74 | ex20_c23 | ucCaggAauggAaauTcc | 156212 | 156229 | 6336.72 | 19 |

In sequences shown in the Table, capital letters represent ENA and small letters 2'-OMe-RNA. For "Start" and "End", respective nucleotide numbers in *Homo sapiens* collagen type IV alpha 5 chain (COL4A5) (NCBI-GenBank accession No. NG_011977) are shown.

Molecular weights in the Table show values as measured by negative-ion ESI mass spectrometry.

As used herein, $A^t$, $G^t$, $5meC^t$, $C^t$, $T^t$, $U^t$, $A^p$, $G^p$, $5meC^p$, $C^p$, $T^p$, $U^p$, $A^s$, $G^s$, $5meC^s$, , $C^s$, $T^s$, $U^s$, $A^{m1t}$, $G^{m1t}$, $C^{m1t}$, $5meC^{m1t}$, $U^{m1t}$, $A^{m1p}$, $G^{m1p}$, $C^{m1p}$, $5meC^{m1p}$, $U_{m1p}$, $A^{m1s}$, $G^{m1s}$, $C^{m1s}$, $5meC^{m1s}$, $U^{m1s}$, $A^{2t}$, $G^{2t}$, $C^{2t}$, $T^{2t}$, $A^{e2p}$, $G^{e2p}$, $C^{e2p}$, $T^{e2p}$, $A^{e2s}$, $G^{e2s}$, $C^{e2s}$, $T^{e2s}$, $A^{1t}$, $G^{1t}$, $C^{1t}$, $T^{1t}$, $A^{e1p}$, $G^{e1p}$, $C^{e1p}$, $T^{e1p}$, $A^{e1s}$, $G^{e1s}$, $C^{e1s}$, $T^{e1s}$, $A^{m2t}$, $G^{m2t}$, $5meC^{m2t}$, $T^{m2t}$, $A^{m2p}$, $G^{m2p}$, $5mC^{m2p}$, $T^{m2p}$, $A^{m2s}$, $G^{m2s}$, $5mC^{m2s}$ and $T^{m2s}$ represent groups with the following structures, respectively.

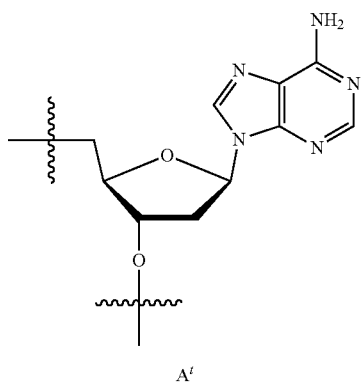

$A^t$

-continued
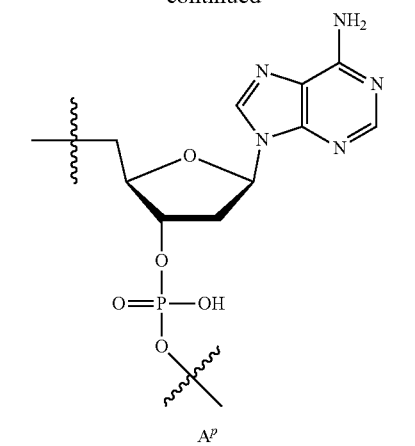
A$^p$
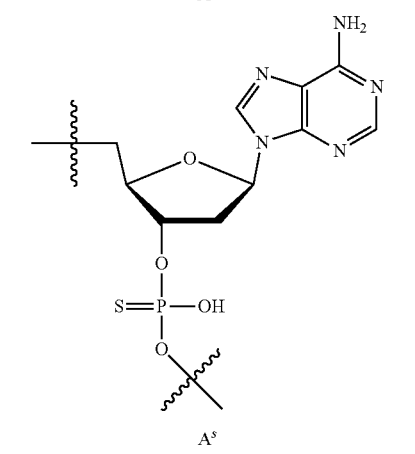
A$^s$
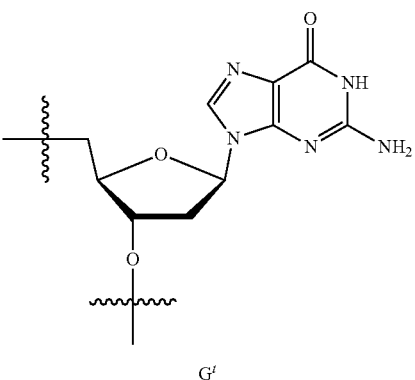
G$^t$
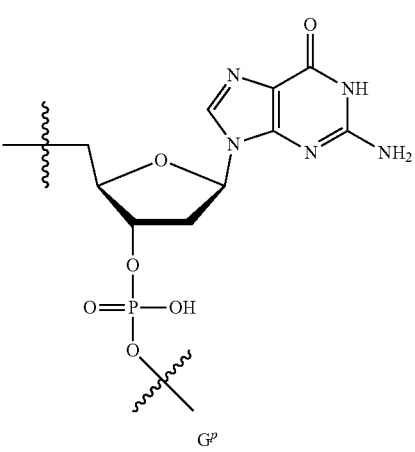
G$^p$
-continued
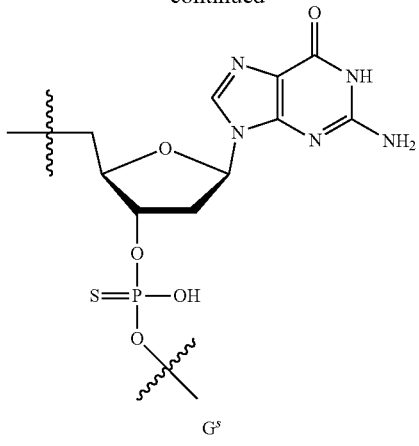
G$^s$
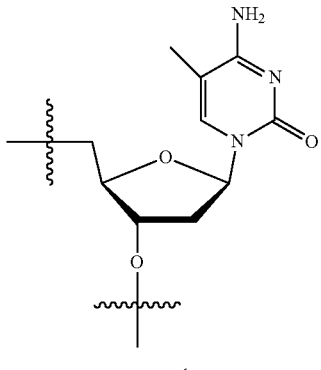
5meC$^t$
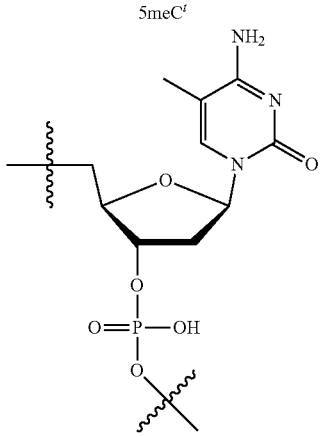
5meC$^p$
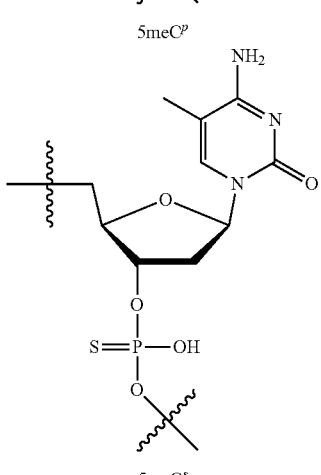
5meC$^s$ -continued
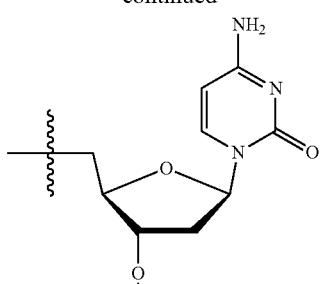
$C^t$
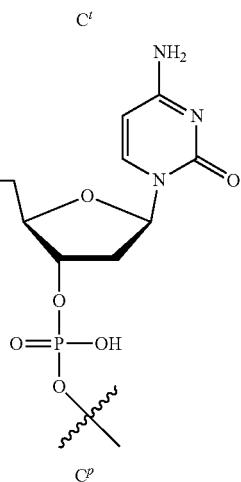
$C^p$
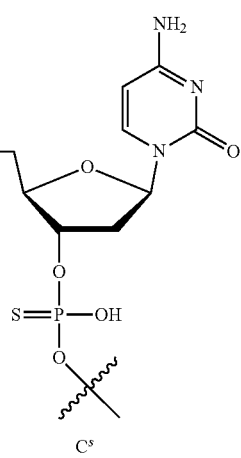
$C^s$
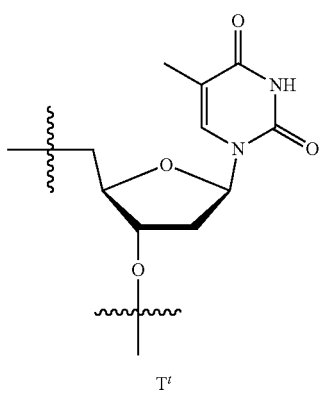
$T^t$
-continued
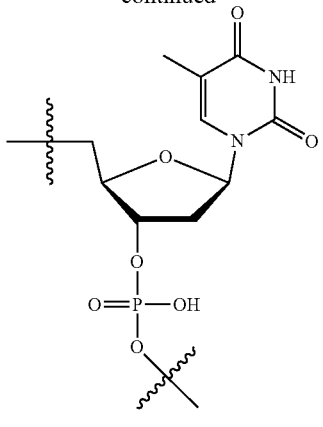
$T^p$
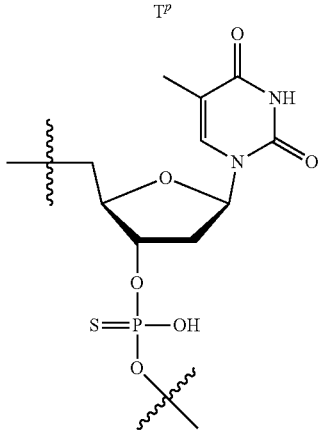
$T^s$
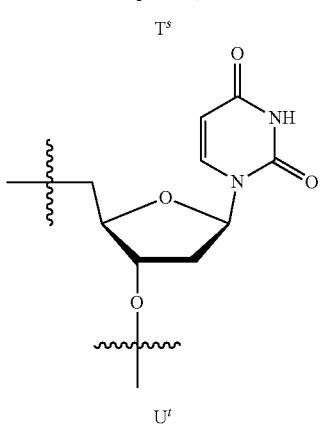
$U^t$
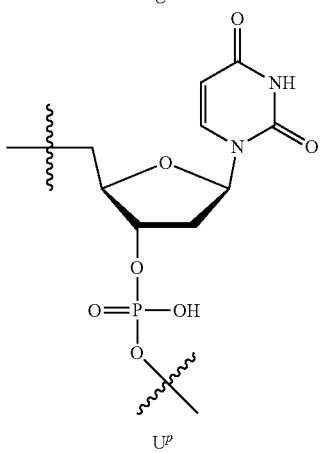
$U^p$

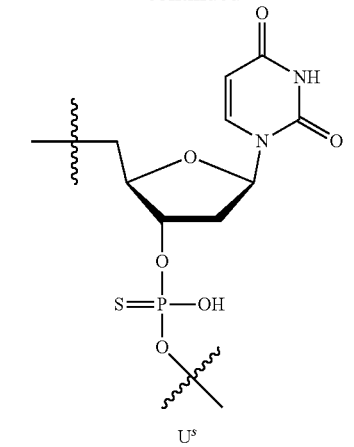
U^s
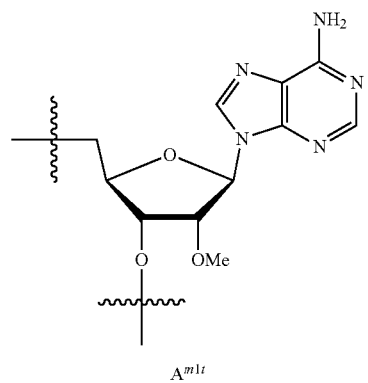
A^{m1t}
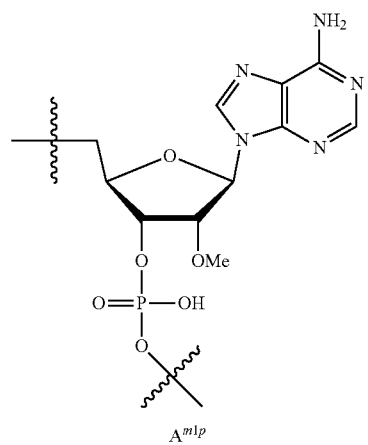
A^{m1p}
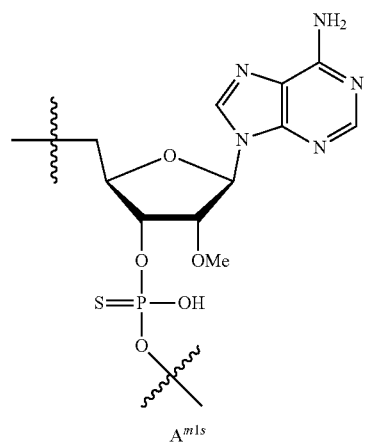
A^{m1s}
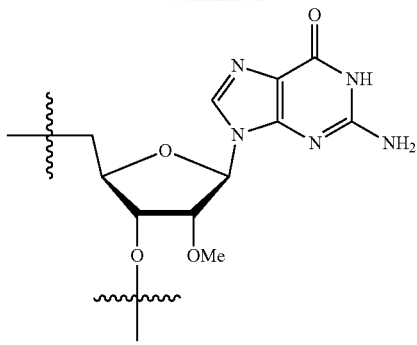
G^{m1t}
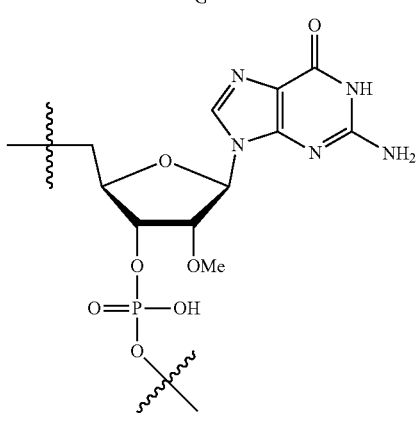
G^{m1p}
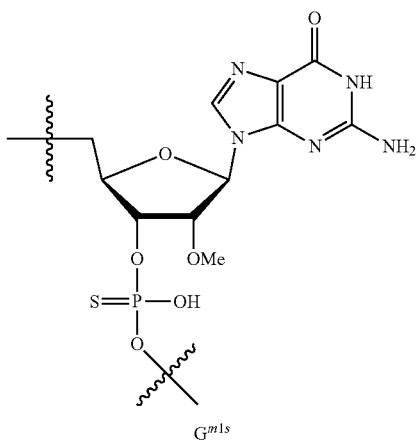
G^{m1s}
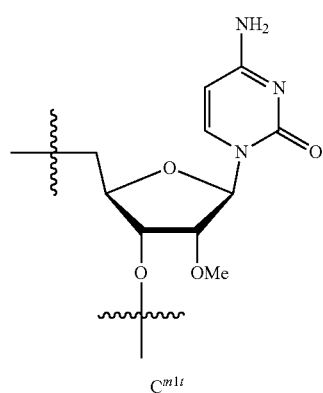
C^{m1t}

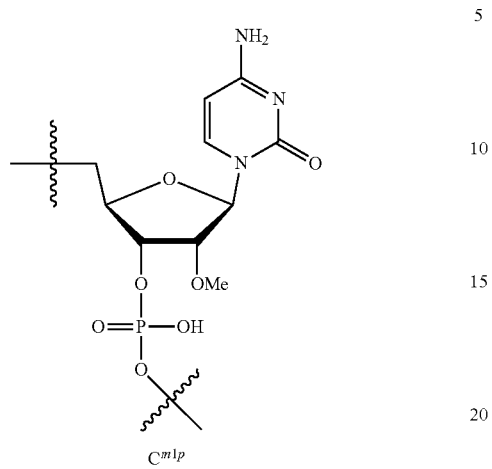
C^{m1p}
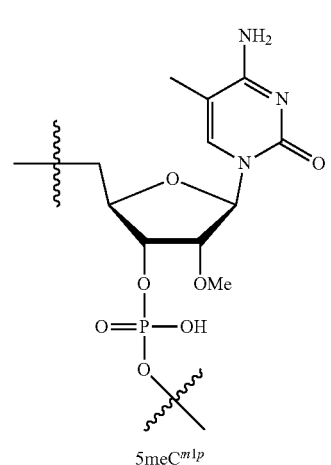
5meC^{m1p}
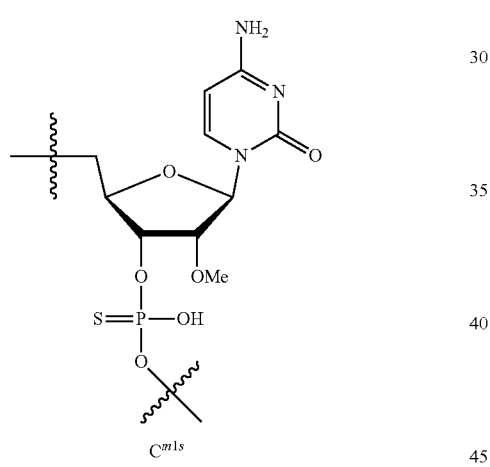
C^{m1s}
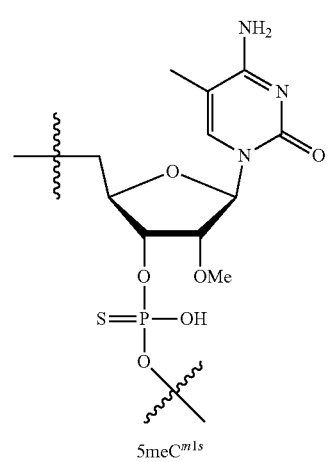
5meC^{m1s}
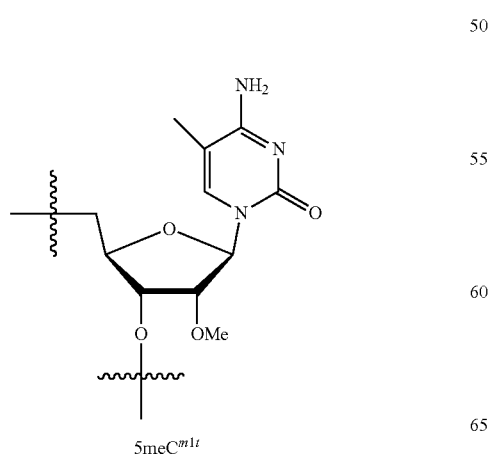
5meC^{m1t}
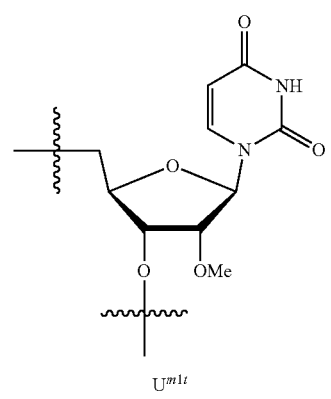
U^{m1t}

-continued
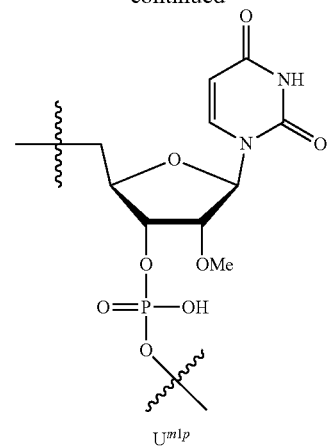
U$^{m1p}$
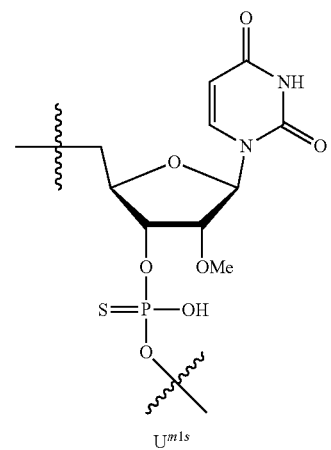
U$^{m1s}$
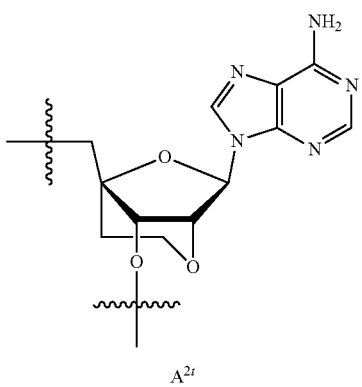
A$^{2t}$
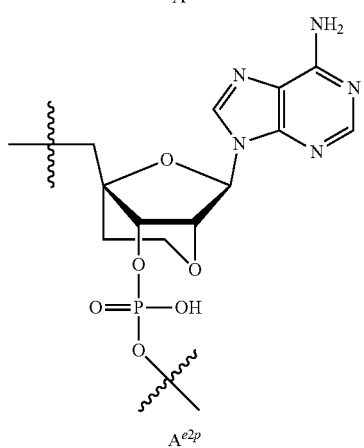
A$^{e2p}$
-continued
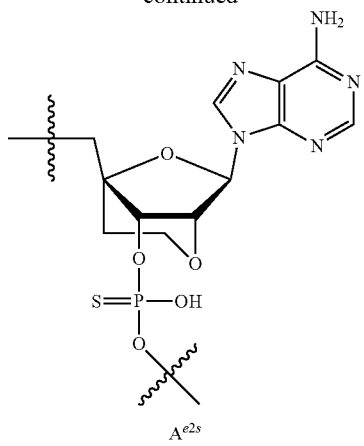
A$^{e2s}$
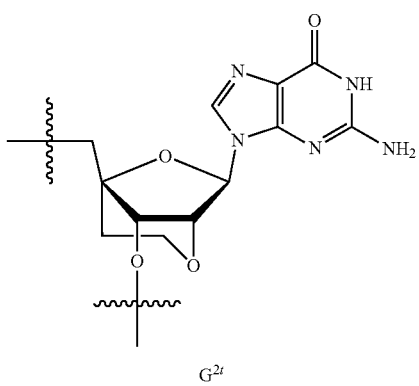
G$^{2t}$
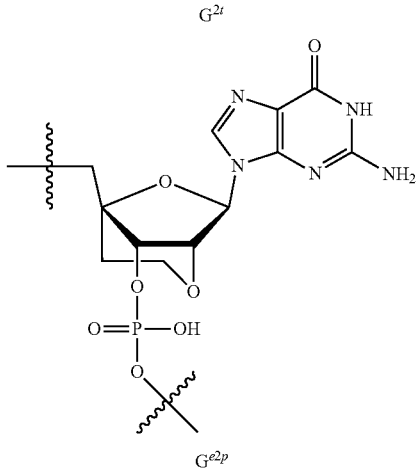
G$^{e2p}$
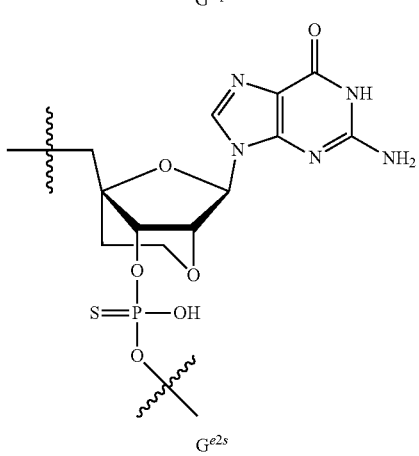
G$^{e2s}$ -continued
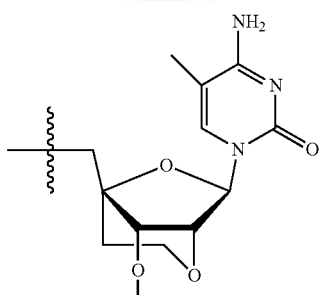
C²ᵗ
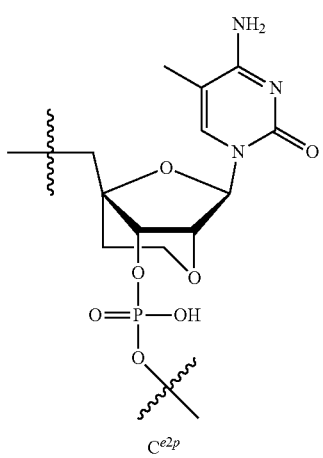
Cᵉ²ᵖ
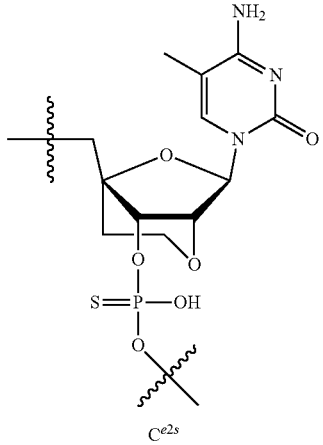
Cᵉ²ˢ
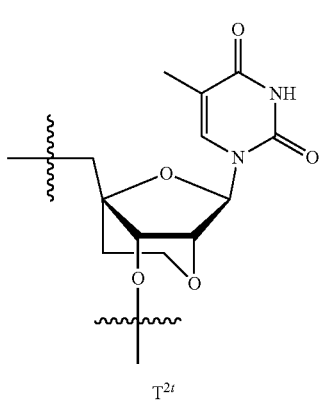
T²ᵗ
-continued
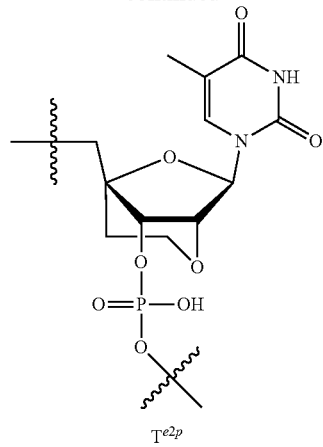
Tᵉ²ᵖ
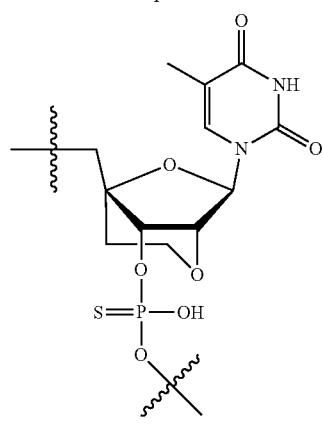
Tᵉ²ˢ
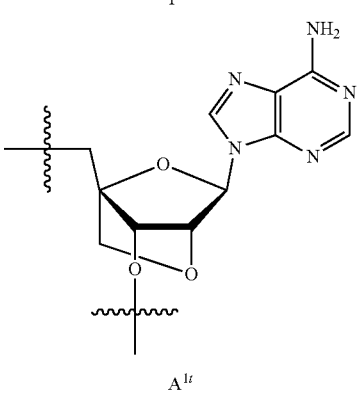
Aˡᵗ
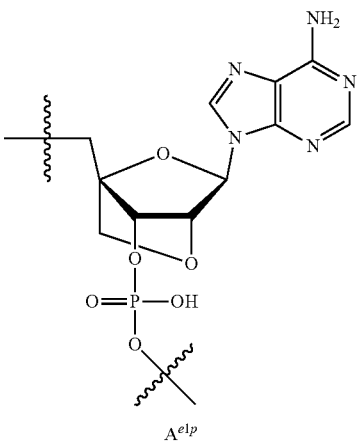
Aᵉ¹ᵖ

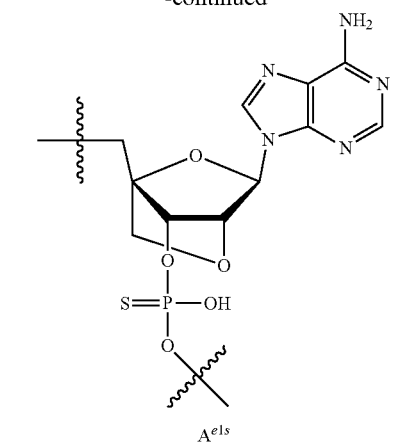
A^els
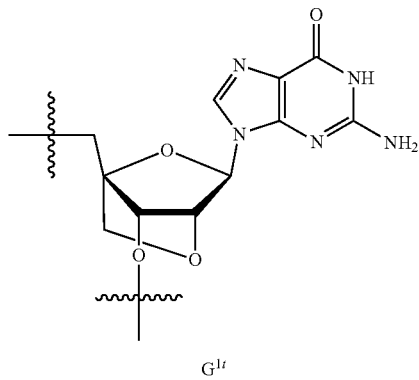
G^lt
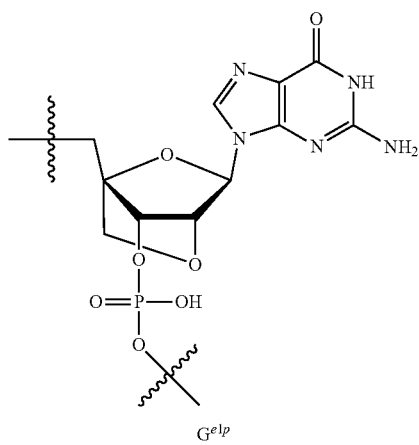
G^elp
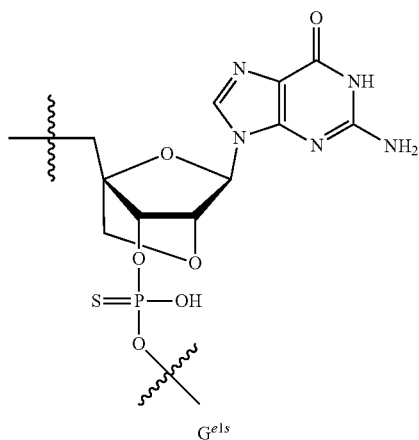
G^els
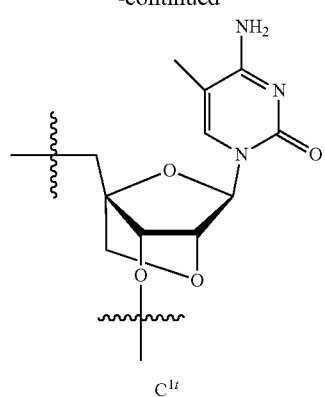
C^lt
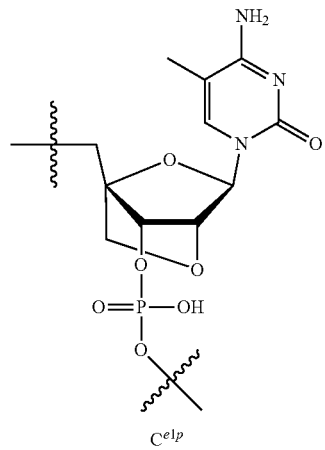
C^elp
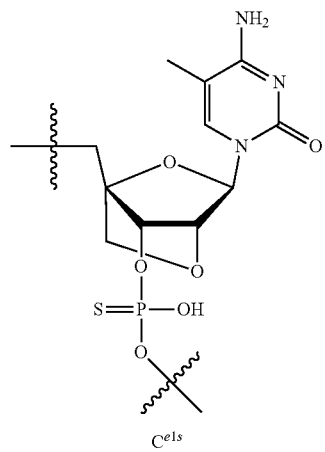
C^els
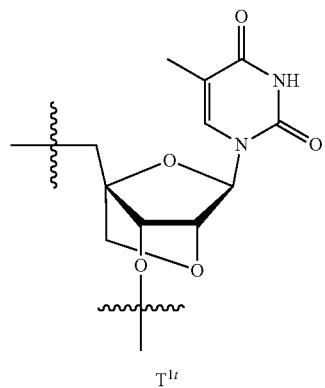
T^lt

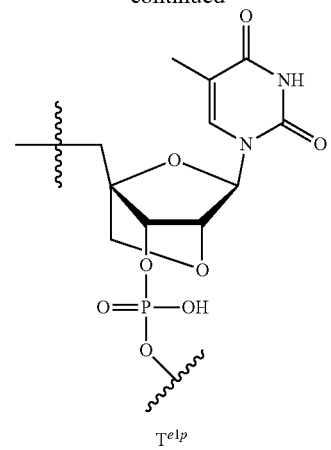
T$^{e1p}$
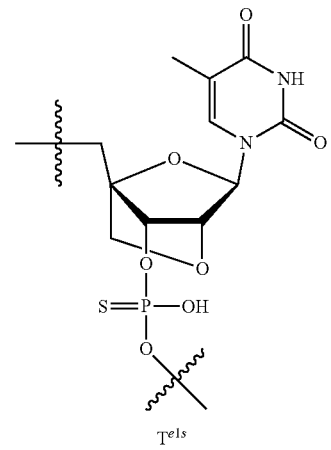
T$^{e1s}$
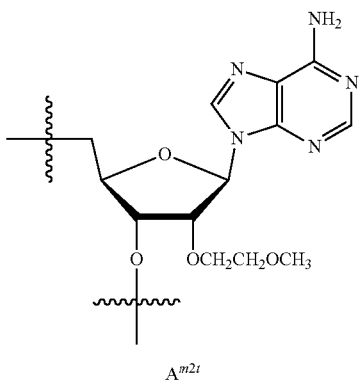
A$^{m2t}$
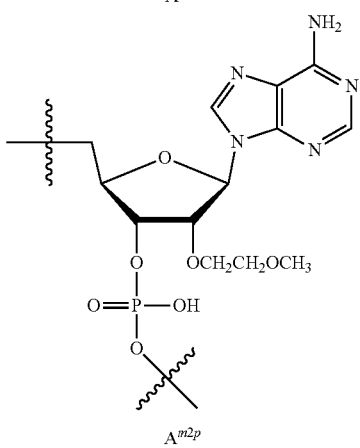
A$^{m2p}$
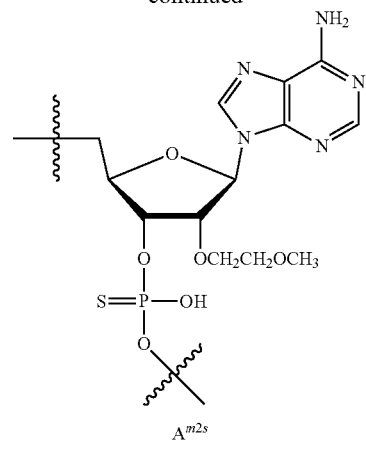
A$^{m2s}$
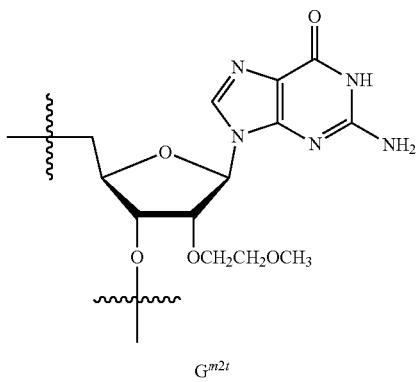
G$^{m2t}$
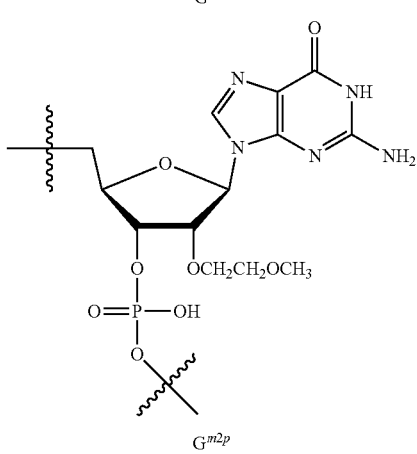
G$^{m2p}$
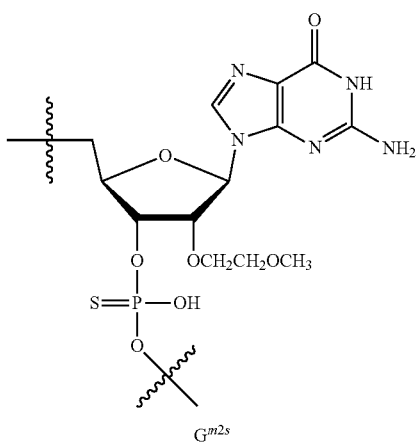
G$^{m2s}$

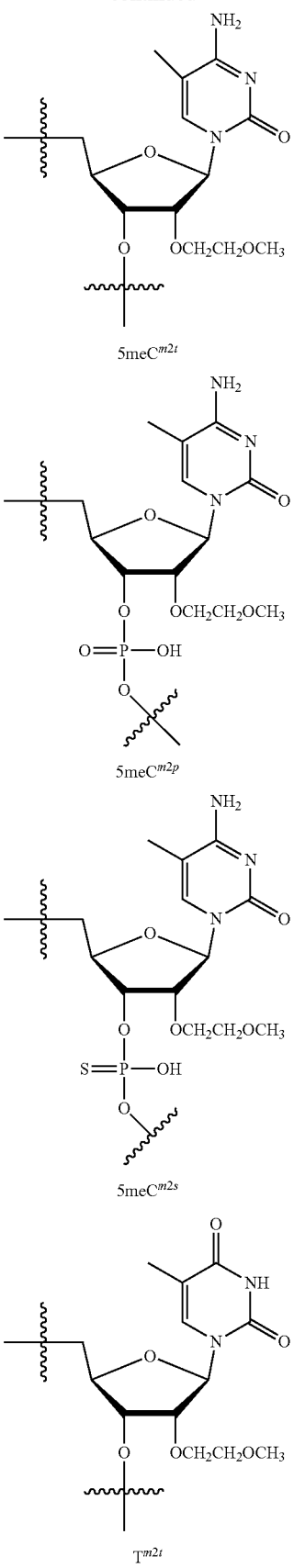

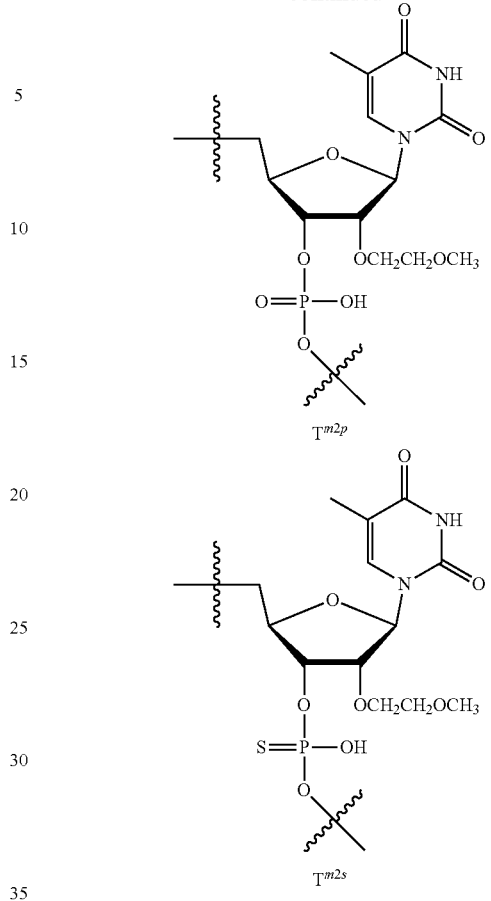

Test Example 1

Analysis of the Exon Skipping Induction Capacity of ENA Oligonucleotide

Culture of HMVECs (Human Dermal Microvascular Endothelial Cells)

HMVECs were cultured as described below.

Normal neonate (single)-derived dermal microvascular endothelial cells HMVEC (CC-2813; Lonza) were cultured in a maintenance medium (EGM-2MV; CC-3202; Lonza). Cells were subcultured at a seeding density of $3.7 \times 10^5/10$ cm dish. For experiments, cells up to 6 passages were used. Cells were seeded on 96 well plates at $2-5 \times 10^3$ cells/well, and the medium was exchanged with a fresh maintenance medium on the next day. Then, oligonucleotides prepared in Examples were introduced as described later.

Preparation of a Primary Culture System for Urine Exfoliated Cells

A primary culture system for urine exfoliated cells was prepared as described below.

A urine sample (about 100 ml) was collected from a patient who had been genetically diagnosed as having X-linked Alport syndrome. The sample was centrifuged (1,400 rpm×10 min) to discard the supernatant. The resultant cell pellets were washed with cold PBS twice. The cell pellets were suspended in a maintenance medium (EGM-MV (Lonza); 20% FBS, penicillin (100 U/ml), streptomycin (1 mg/ml) and rifampicin (8 μg/ml)) and incubated in a 37° C., 5% $CO_2$ incubator. After the second passage, cells were cultured in the maintenance medium without rifampicin.

Directed Differentiation into Renal Glomerular Epithelial Cells (Podocytes)

Differentiation from patient-derived urine exfoliated cells into renal glomerular epithelial cells (podocytes) was induced as described below.

Cells were seeded on 96 well plates at a density of $1\times10^4$ cells/well, and the medium was exchanged with a medium for directed differentiation (DMEM/F12, 5% FBS, 1×ITS supplement, 12.5 μM retinoic acid) on the next day (day 0 of directed differentiation). From that time on, the medium was exchanged every three days. At day 8 of directed differentiation, oligonucleotides prepared in Examples were introduced as described later.

Transfection of Oligonucleotides Prepared in Examples

Oligonucleotides prepared in Examples were transfected as described below.

The following Solution A and Solution B were prepared and mixed.

| | | |
|---|---|---|
| Solution A: | Opti-MEM Medium (Thermofisher) | 20 μl |
| | Compound prepared in Example (20 μM) | 1 μl (final concentration: 50 nM) |
| Solution B: | Opti-MEM Medium | 20 μl |
| | Lipofectamine RNAiMAX (Thermofisher) | 1.2 μl |

The above mixed solution was incubated for 5 min at room temperature. The thus prepared solution was added in portions of 10 μl/well, followed by incubation for 48 hrs.

RNA Extraction

RNA was extracted as described below.

The cells incubated for 48 hrs after oligonucleotide transfection were washed once with cold PBS. The cell lysis solution contained in SuperPrep Cell Lysis Kit & RT Kit for qPCR (TOYOBO) was added in portions of 50 μl/well. After shaking for 30 sec, cells were incubated at room temperature for 5 min. The quenching solution contained in SuperPrep Cell Lysis Kit & RT Kit for qPCR was added in portions of 10 μl/well. After shaking for 30 sec, cells were incubated at room temperature for 2 min. A total of 60 μl of cell lysate was recovered and used in the reverse transcription reaction described below.

Reverse Transcription Reaction

Reverse transcription was performed as described below.

The reverse transcription master mix (32 μl) and the cell lysis solution (8 μl) both contained in SuperPrep Cell Lysis Kit & RT Kit for qPCR were mixed. Reverse transcription was performed as follows: 37° C. 15 min, 50° C. 5 min, 98° C. 5 min and 4° C. hold. The final products were stored at −30° C.

PCR Reaction and Analysis of Fragment Sequences

PCR reaction and analysis of fragment sequences were performed as described below.

PCR reaction solution was prepared from the components listed below.

| | |
|---|---|
| Reverse transcription products | 1-1.5 μl |
| Sterilized water | 13.9 μl |
| 10x Buffer (attached to TAKARA Ex Taq) | 2 μl |
| dNTP (attached to TAKARA Ex Taq) | 2 μl |
| Forward primer (10 μM) | 0.5 μl |
| Reverse primer (10 μM) | 0.5 μl |
| Ex Taq (TAKARA) | 0.1 μl |
| Total | 20 μl |

PCR reaction was performed as follows: 94° C. 5 min, (94° C. 30 sec, 60° C. 30 sec, 72° C. 30 sec)×30-38 cycles, 72° C. 5 min, and 4° C. hold.

Primers for analysis were designed as follows.

```
1) For analysis of expression of entire COL4A5
(Exon 1-7)
Forward (5'-3'):
                                        (SEQ ID NO: 29)
cagaggctgcggcttgctat Reverse (5'-3'):
                                        (SEQ ID NO: 30)
ccacgttctccatggttcca 2) For analysis of Exon 20 skipping (Exon 17-22)
Forward (5'-3'):
                                        (SEQ ID NO: 31)
gggatggtgaaaagggccaaaaag Reverse (5'-3'):
                                        (SEQ ID NO: 32)
cctttgtcacctttcactccttgt 3) For analysis of Exon 24 skipping (Exon 21-26)
Forward (5'-3'):
                                        (SEQ ID NO: 33)
caaggagtgaaaggtgacaaaggt Reverse (5'-3'):
                                        (SEQ ID NO: 34)
ccattaggacctggtattcctg 4) For analysis of endogenous control gene
(GAPDH)
Forward (5'-3'):
                                        (SEQ ID NO: 35)
ccatcattgacctcaac Reverse (5'-3'):
                                        (SEQ ID NO: 36)
ttcacacccatgacgaac
```

PCR products were electrophoresed in 1.8% agarose gel containing ethidium bromide and analyzed. Each fragment was extracted from the gel with PCR purification kit (QIAGEN), followed by sequencing with BigDye v1.1. The nucleotide sequence was confirmed with ABI PRISM 3130 Genetic Analyzer (Applied Biosystems) and CLC Main Workbench 6 (CLC bio).

Immunofluorescent Staining of Differentiated Podocytes

Immunofluorescent staining was performed as described below.

Briefly, differentiated podocytes were washed with PBS and fixed with 4% paraformaldehyde+4% sucrose/PBS at room temperature for 10 min. After washing with PBS three times, permeabilization was performed with 0.1% Triton X-100/PBS at room temperature for 5 min. After washing with PBS three times, podocytes were blocked with 5% fetal bovine serum/PBS. Primary antibodies (rat anti-COL4A5 H53 antibody kindly provided by Dr. Yoshikazu Satoh, Shigei Medical Research Institute; mouse anti-Synaptopodin antibody for which a mouse hybridoma supernatant kindly provided by Dr. Eishinn Yaoita, Kidney Research Center, Niigata University Graduate School of Medical and Dental Sciences was used) were reacted at 4° C. overnight. After washing with PBS three times, secondary antibodies (Alexa Fluor 488 goat ant-rat IgG; Alexa Fluor 555 goat anti-mouse IgG) were reacted at room temperature for 1 hr. After washing with PBS three times, Hoechst 33342 was reacted at room temperature for 10 min for nuclear staining. After being placed under a coverslip, podocytes were observed under a fluorescence microscope.

Exon Skipping Caused by the Compounds of Examples, in HMVEC or Alport Syndrome Patient-Derived Urine Exfoliated Cells As shown in FIG. 2, when skipping of exon 24 by exon 24-targeting oligonucleotides (from Examples 1 to 27) was examined in HMVEC, skipping of exon 24 was observed with oligonucleotides from Examples 1 to 27 (FIG. 2A). Oligonucleotides from Example 1, Example 2, Example 3 and Example 13 showed particularly high skipping efficiencies. Further, when sequence analysis of fragments observed on gel was performed, fragment 2 was confirmed to have a sequence involving the skipping of exon 24 (FIGS. 2B and 2C).

As shown in FIG. 3, urine exfoliated cells derived from an Alport syndrome patient with a mutation in exon 24 were differentiated into COL4A5 expressing renal glomerular epithelial cells (podocytes); exon 24-targeting three oligonucleotides (from Examples 1 to 3) were introduced (50 nM each) and their effects were confirmed. Briefly, expressions of COL4A5 and a differentiated podocyte marker, Synaptopodin (goat anti-Synaptopodin antibody; Santa Cruz) were evaluated. Compared to non-transfected cells (Mock), expression of COL4A5 protein (green) was increased in oligonucleotide-transfected cells. Moreover, an increase in expression of the differentiated podocyte marker Synaptopodin (red) was also confirmed in the oligonucleotide-transfected cells. These results suggested that the introduction of oligonucleotides not only contributes to an increased expression of COL4A5 protein but possibly also affects the differentiation capacity of podocytes.

Figure 4:
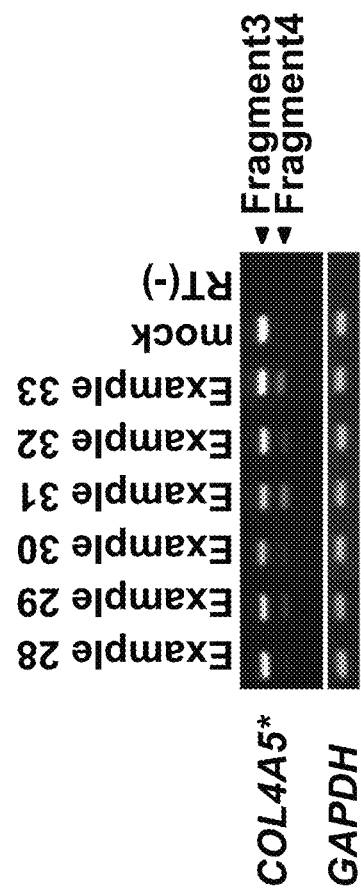
FIG. 4 A drawing showing the effects of compounds from Examples 28 to 33 on exon 20 of COL4A5.

As shown in FIG. 4, when skipping of exon 20 by exon 20-targeting oligonucleotides (from Examples 28 to 33) was examined using HMVECs (cells capable of high-yield expression of COL4A5), skipping of exon 20 was observed with oligonucleotides from Examples 28 to 33. Oligonucleotide from Example 31 showed a particularly high skipping efficiency.

As shown in FIG. 5, when skipping of exon 20 by exon 20-targeting oligonucleotides (from Examples 34 to 51) was examined using HMVECs (cells capable of high-yield expression of COL4A5), skipping of exon 20 was observed with oligonucleotides from Examples 34 to 51 (FIG. 5A). Oligonucleotide from Example 43 showed a particularly high skipping efficiency.

Figure 6:
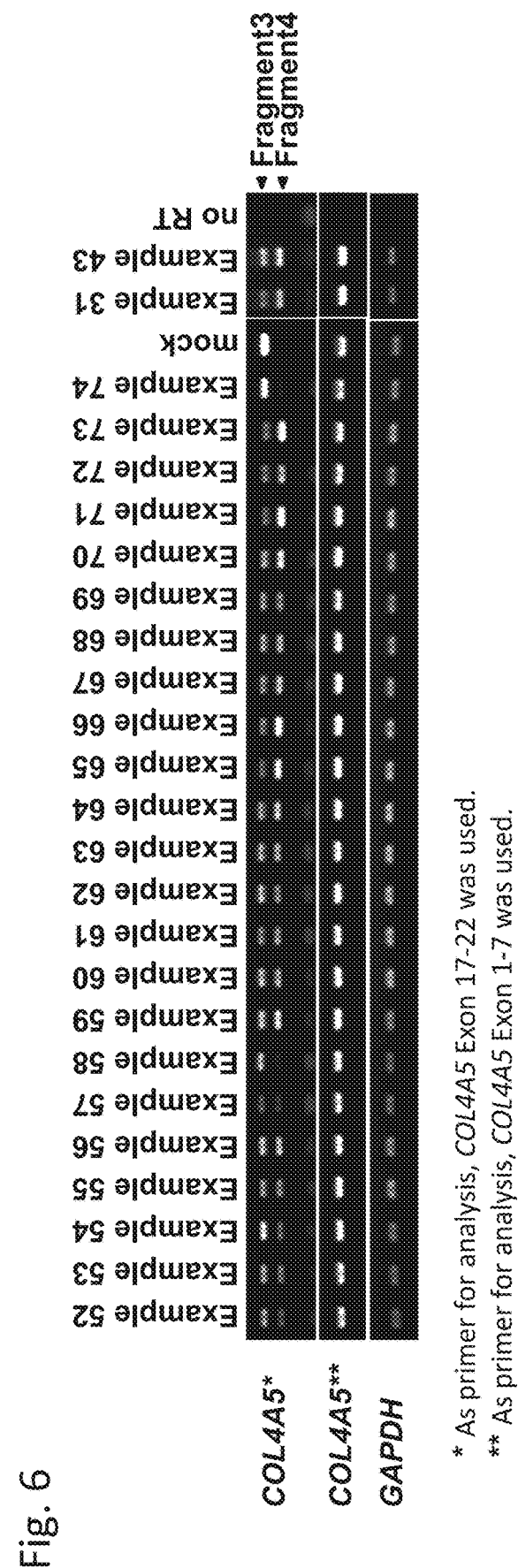
FIG. 6 A drawing showing the effects of compounds from Examples 31, 43 and 52 to 74 on exon 20 of COL4A5.

As shown in FIG. 6, when skipping of exon 20 by exon 20-targeting oligonucleotides (from Examples 52 to 74) was examined using HMVECs (cells capable of high-yield expression of COL4A5), skipping of exon 20 was observed with every oligonucleotide tested.

As shown in FIG. 7, urine exfoliated cells derived from an Alport syndrome patient with a mutation in exon 20 were differentiated into COL4A5 expressing renal glomerular epithelial cells (podocytes); and skipping of exon 20 by exon 20-targeting oligonucleotides (from Examples 52 to 74) was examined. As a result, skipping of exon 20 was observed with every oligonucleotide examined (FIG. 7A). Further, when sequence analysis of fragments observed on gel was performed, fragment 6 was confirmed to have a sequence involving the skipping of exon 20 (FIGS. 7B and 7C).

Figure 8:
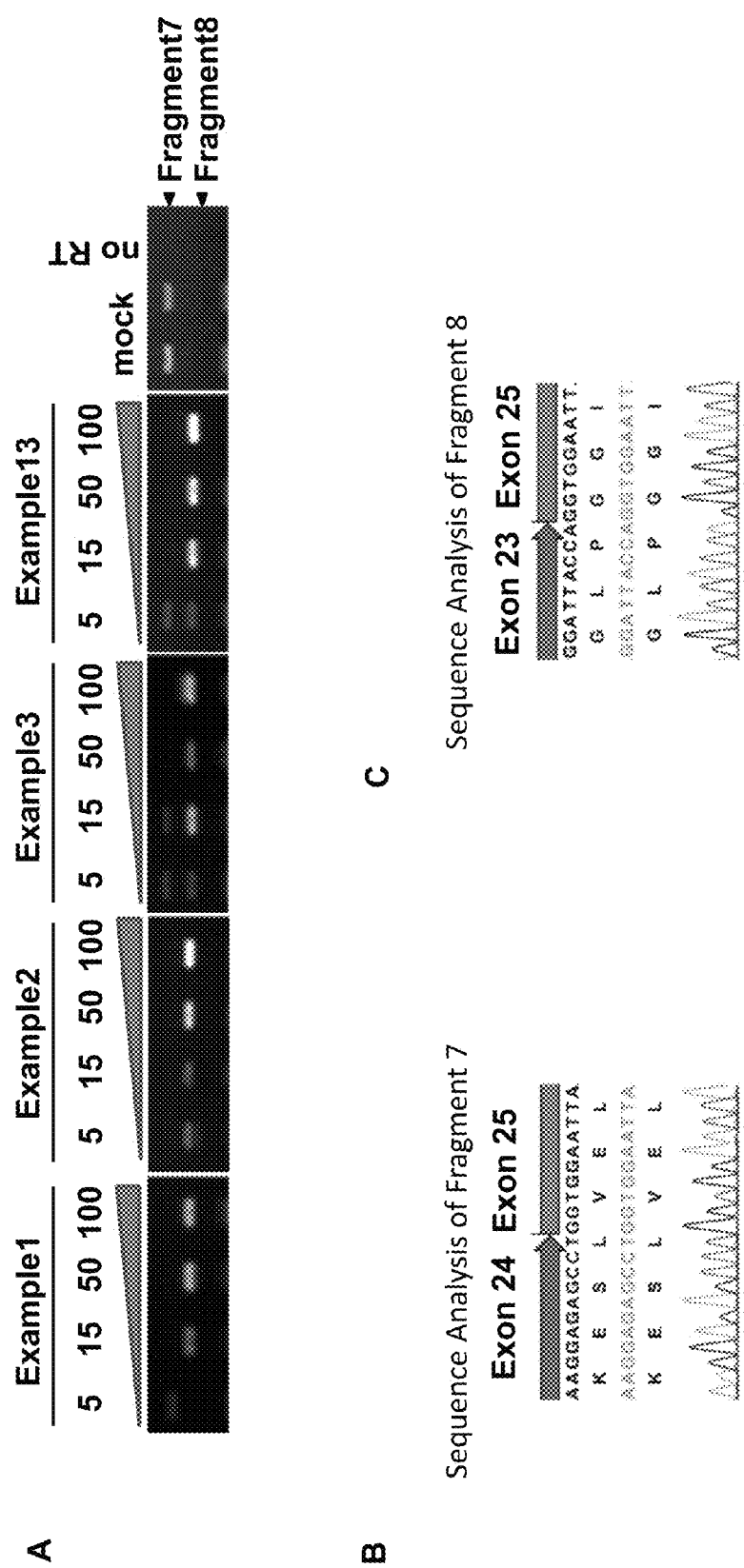
FIG. 8 A part of the sequence of fragment 7 is shown in residues 1-20 of SEQ ID NO:53. A part of the sequence of fragment 8 is shown in residues 3-21 of SEQ ID NO:54. (A) A drawing showing the effects of compounds from Examples 1, 2, 3 and 13 on exon 24 of COL4A5. (B, C) Two drawings, with the left one showing the sequence of fragment 7 before the skipping of exon 24 takes place, and the right one showing the sequence of fragment 8 in which exon 24 has been skipped.

As shown in FIG. 8, urine exfoliated cells from an Alport syndrome patient with a mutation in exon 24 were differentiated into COL4A5 expressing renal glomerular epithelial cells (podocytes); exon 24-targeting oligonucleotides (from Examples 1, 2, 3 and 13) were introduced at 5, 15, 50 or 100 nM each; and skipping of exon 24 was examined. As a result, skipping of exon 24 was observed with every oligonucleotide examined in a concentration dependent manner (FIG. 8A). Further, when sequence analysis of fragments observed on gel was performed, fragment 8 was confirmed to have a sequence involving the skipping of exon 24 (FIGS. 8B and 8C).

Examples 75 to 98

Compounds of Examples 75 to 98 were also synthesized in the same manner as described in Example 4. The sequences and data of the compounds from Examples 75 to 98 are summarized in Table 5 below.

TABLE 5

| Example | Designation | Sequence (5'-3') | Start | End | Molecular Weight | SEQ ID NO: |
|---|---|---|---|---|---|---|
| 75 | ex24_c25 | cCcTggcaaTccauCcTg | 162604 | 162621 | 6278.72 | 37 |
| 76 | ex24_c26 | cCcTggcaaTccauCcTg | 162604 | 162621 | 6278.72 | 37 |
| 77 | ex24_c27 | cCcuggCaaTccaTccTg | 162604 | 162621 | 6278.73 | 37 |
| 78 | ex24_c28 | cCcTggcaauccauCcTg | 162604 | 162621 | 6252.72 | 37 |
| 79 | ex24_c29 | cCcuggCaaucCauccTg | 162604 | 162621 | 6252.72 | 37 |
| 80 | ex24_c30 | ccCuggCaaucCauccCug | 162604 | 162621 | 6252.70 | 37 |
| 81 | ex24_c31 | cCcTggcaauccauCcTg | 162604 | 162621 | 6252.72 | 37 |
| 82 | ex24_c32 | CccuggCaaucCauccTg | 162604 | 162621 | 6252.70 | 37 |
| 83 | ex24_c33 | CcTggcaaTccauccTgT | 162603 | 162620 | 6279.67 | 38 |
| 84 | ex24_c34 | CcTggcaauCcauccTgT | 162603 | 162620 | 6279.71 | 38 |
| 85 | ex24_c35 | CcTggcaaucCauccTgT | 162603 | 162620 | 6279.71 | 38 |
| 86 | ex24_c36 | CcTggcaauccauccTgT | 162603 | 162620 | 6253.71 | 38 |
| 87 | ex24_c37 | CcuggCaauccaTccugT | 162603 | 162620 | 6253.68 | 38 |
| 88 | ex24_c38 | ccTggcAauccAuccTgu | 162603 | 162620 | 6225.70 | 38 |

TABLE 5-continued

| Example | Designation | Sequence (5'-3') | Start | End | Molecular Weight | SEQ ID NO: |
|---|---|---|---|---|---|---|
| 89 | ex24_c39 | ccTggcaaTccaTccugT | 162603 | 162620 | 6253.69 | 38 |
| 90 | ex24_c40 | cCuggCaauccaTccugT | 162603 | 162620 | 6253.69 | 38 |
| 91 | ex24_c41 | CuggCaaucCaucCuguC | 162602 | 162619 | 6279.70 | 39 |
| 92 | ex24_c42 | CuggCaauCcaucCuguC | 162602 | 162619 | 6279.71 | 39 |
| 93 | ex24_c43 | cTggCaauCcaucCugTc | 162602 | 162619 | 6279.71 | 39 |
| 94 | ex24_c44 | CuggcAauccauCcuguC | 162602 | 162619 | 6239.63 | 39 |
| 95 | ex24_c45 | CuggcaAuccaTccuguC | 162602 | 162619 | 6239.68 | 39 |
| 96 | ex24_c46 | cTggcaAuccaTccugTc | 162602 | 162619 | 6239.68 | 39 |
| 97 | ex24_c47 | cTggcaaTccaTccugTc | 162602 | 162619 | 6253.69 | 39 |
| 98 | ex24_c48 | cTggcaaTccauccTgTc | 162602 | 162619 | 6253.71 | 39 |

In sequences shown in the Table, capital letters represent ENA and small letters 2'-OMe-RNA. For "Start" and "End", respective nucleotide numbers in *Homo sapiens* collagen type IV alpha 5 chain (COL4A5) (NCBI-GenBank accession No. NG_011977) are shown. Molecular weights in the Table show values as measured by negative-ion ESI mass spectrometry.

Examples 99 to 139

Compounds of Examples 99 to 139 were also synthesized in the same manner as described in Example 4. The sequences and data of the compounds from Examples 99 to 139 are summarized in Table 6 below.

TABLE 6

| Example | Designation | Sequence (5'-3') | Start | End | Molecular Weight | SEQ ID NO: |
|---|---|---|---|---|---|---|
| 99 | ex21_010 | cTugGagTccTuuAucAc | 156703 | 156686 | 6265.65 | 40 |
| 100 | ex21_011 | gGagTccTuuAucAccTg | 156700 | 156683 | 6304.68 | 41 |
| 101 | ex21_b08 | cCuuGgaGucCuuTauCa | 156704 | 156687 | 6279.59 | 42 |
| 102 | ex21_b09 | uTggAguCcuTuaTcaCc | 156702 | 156685 | 6293.67 | 43 |
| 103 | ex21_b10 | uGgaGucCuuTauCacCu | 156702 | 156684 | 6279.67 | 44 |
| 104 | ex21_c01 | cCuuggAguccTuuauCa | 156704 | 156687 | 6241.65 | 42 |
| 105 | ex21_c02 | ccTuggAguccTuuaTca | 156704 | 156687 | 6241.64 | 42 |
| 106 | ex21_c03 | ccuTggAguccTuuAuca | 156704 | 156687 | 6227.63 | 42 |
| 107 | ex21_c04 | ccTuggagTccuTuaTca | 156704 | 156687 | 6255.57 | 42 |
| 108 | ex21_c05 | CcTuggagTccuuuaTcA | 156704 | 156687 | 6267.66 | 42 |
| 109 | ex21_c06 | CcTuggaguCcuuuaTcA | 156704 | 156687 | 6267.64 | 42 |
| 110 | ex21_c07 | CcTuggagucCuuuaTcA | 156704 | 156687 | 6267.65 | 42 |
| 111 | ex21_c08 | cCuTggagTccuuuAuCa | 156704 | 156687 | 6267.66 | 42 |
| 112 | ex21_c09 | cCuTggaguCcuuuAuCa | 156704 | 156687 | 6267.65 | 42 |
| 113 | ex21_c10 | cTuggAguccuuTaucAc | 156703 | 156686 | 6227.62 | 40 |
| 114 | ex21_c12 | CuTggaguCcuuuauCaC | 156703 | 156686 | 6281.64 | 40 |
| 115 | ex21_c13 | CuTggagucCuuuauCaC | 156703 | 156686 | 6281.67 | 40 |
| 116 | ex21_c14 | CuTggaguccTuuauCaC | 156703 | 156686 | 6281.66 | 40 |
| 117 | ex21_c15 | uTggagTccuuTaucAcc | 156702 | 156685 | 6255.66 | 43 |
| 118 | ex21_c16 | uTggAguccuuuaTcaCc | 156702 | 156685 | 6241.63 | 43 |

TABLE 6-continued

| Example | Designation | Sequence (5'-3') | Start | End | Molecular Weight | SEQ ID NO: |
|---|---|---|---|---|---|---|
| 119 | ex21_c17 | TuggAgucCuuuaTcacC | 156702 | 156685 | 6267.62 | 43 |
| 120 | ex21_c18 | TuggAgucCuuuaTcacC | 156702 | 156685 | 6267.58 | 43 |
| 121 | ex21_c19 | uTggAgucCuuuaTcaCc | 156702 | 156685 | 6267.65 | 43 |
| 122 | ex21_c20 | uTggAguccTuuaTcaCc | 156702 | 156685 | 6267.58 | 43 |
| 123 | ex21_c21 | uTggagTccTuuaTcaCc | 156702 | 156685 | 6281.67 | 43 |
| 124 | ex21_c22 | uTggagTccuTuaTcaCc | 156702 | 156685 | 6281.66 | 43 |
| 125 | ex21_c23 | TuggagTccTuuaTcacC | 156702 | 156685 | 6282.65 | 43 |
| 126 | ex21_c24 | uggAguCcuuuAucAccu | 156701 | 156684 | 6213.62 | 44 |
| 127 | ex21_c25 | uggAguCcuuuAucAccu | 156701 | 156684 | 6227.63 | 44 |
| 128 | ex21_c26 | uggagucCuuTauCacCu | 156701 | 156684 | 6255.61 | 44 |
| 129 | ex21_c27 | TggAguccuuuAucAccT | 156701 | 156684 | 6239.64 | 44 |
| 130 | ex21_c28 | TggAguCcuuuaTcaCcu | 156701 | 156684 | 6267.65 | 44 |
| 131 | ex21_c29 | TggAguccuuuAucAccT | 156701 | 156684 | 6239.63 | 44 |
| 132 | ex21_c30 | TggagucCuuTauCacCu | 156701 | 156684 | 6281.67 | 44 |
| 133 | ex21_c31 | TggagTccuTuauCaccT | 156701 | 156684 | 6281.67 | 44 |
| 134 | ex21_c32 | TggagTccuTuauCacCu | 156701 | 156684 | 6281.68 | 44 |
| 135 | ex21_c33 | uggagTccTuTauCacCu | 156701 | 156684 | 6281.68 | 44 |
| 136 | ex21_c34 | ggAgucCuuuaTcacCug | 156700 | 156683 | 6280.67 | 41 |
| 137 | ex21_c35 | ggAguCcuuTaucAccTg | 156700 | 156683 | 6292.66 | 41 |
| 138 | ex21_c36 | gGagucCuuuaTcaccTg | 156700 | 156683 | 6280.54 | 41 |
| 139 | ex21_c37 | ggAguCcuTuaTcaCcug | 156700 | 156683 | 6306.61 | 41 |

In sequences shown in the Table, capital letters represent ENA and small letters 2'-OMe-RNA. For "Start" and "End", respective nucleotide numbers in *Homo sapiens* collagen type IV alpha 5 chain (COL4A5) (NCBI-GenBank accession No. NG_011977) are shown. Molecular weights in the Table show values as measured by negative-ion ESI mass spectrometry.

Test Example 2

Analysis of the Exon Skipping Induction Capacity of ENA Oligonucleotide

Culture of HMVECs (human dermal microvascular endothelial cells), preparation of a primary culture system for urine exfoliated cells, directed differentiation to renal glomerular epithelial cells (podocytes), transfection of oligonucleotides prepared in Examples, RNA extraction, reverse transcription reaction, PCR reaction and sequence analysis of fragments, and immunofluorescent staining of differentiated podocytes were carried out in the same manner as described in Test Example 1.

Figure 9:
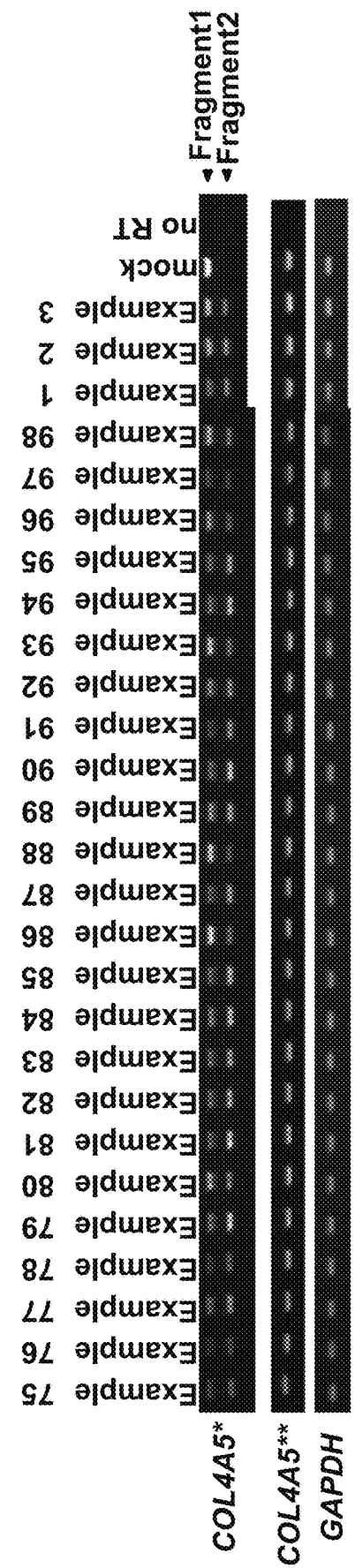
FIG. 9 A drawing showing the effects of compounds from Examples 1 to 3 and 75 to 98 on exon 24 of COL4A5.

Exon Skipping Caused by the Compounds of Examples, in HMVEC or Alport Syndrome Patient-Derived Urine Exfoliated Cells As shown in FIG. 9, when skipping of exon 24 by exon 24-targeting oligonucleotides (from Examples 75 to 98) was examined in HMVEC, fragment 2 showing the skipping of exon 24 was detected (as in FIG. 2) with every one of the oligonucleotides from Examples 75 to 98. Thus, skipping of exon 24 was confirmed.

Figure 10:
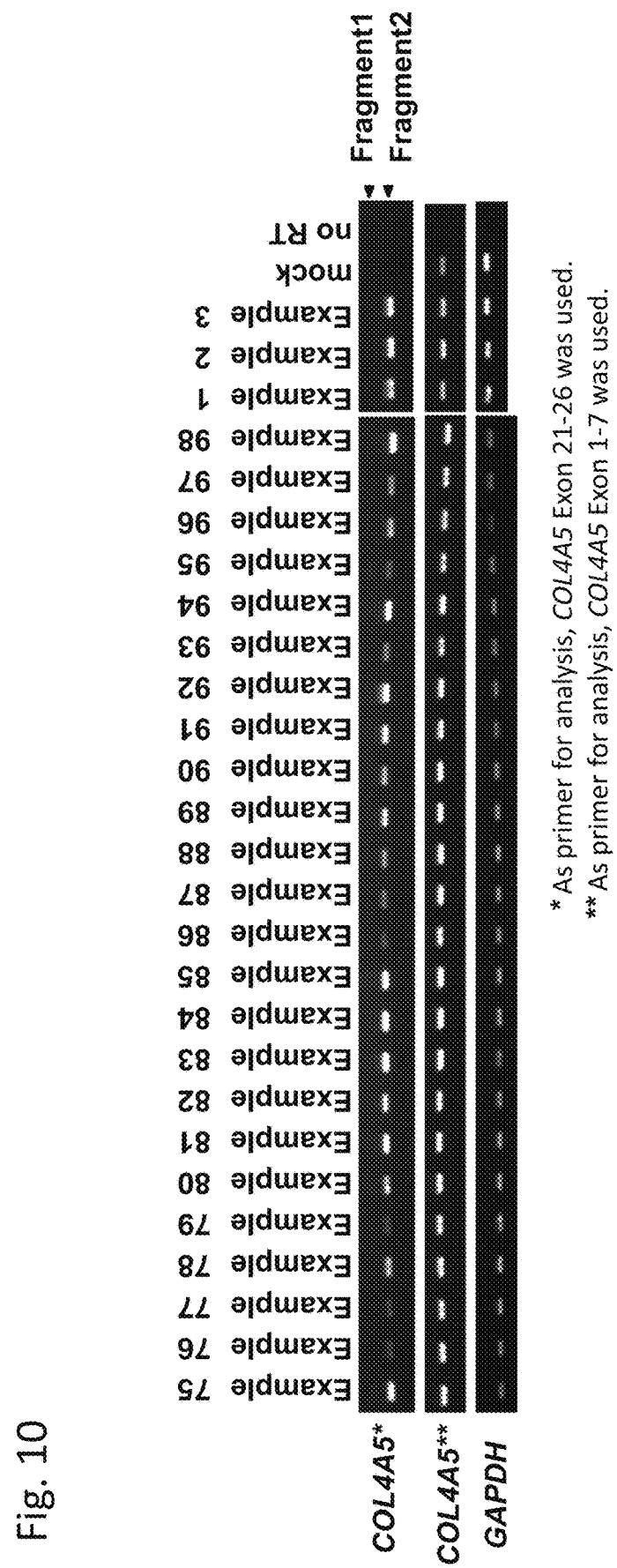
FIG. 10 A drawing showing the effects of compounds from Examples 1 to 3 and 75 to 98 on exon 24 of COL4A5.

As shown in FIG. 10, urine exfoliated cells derived from an Alport syndrome patient with a mutation in exon 24 were differentiated into COL4A5 expressing renal glomerular epithelial cells (podocytes); and skipping of exon 24 was examined with exon 24-targeting oligonucleotides (from Examples 75 to 98). As a result, fragment 2 showing the skipping of exon 24 was detected as in FIG. 2. Thus, skipping of exon 24 was confirmed with every one of the oligonucleotides examined.

Figure 11:
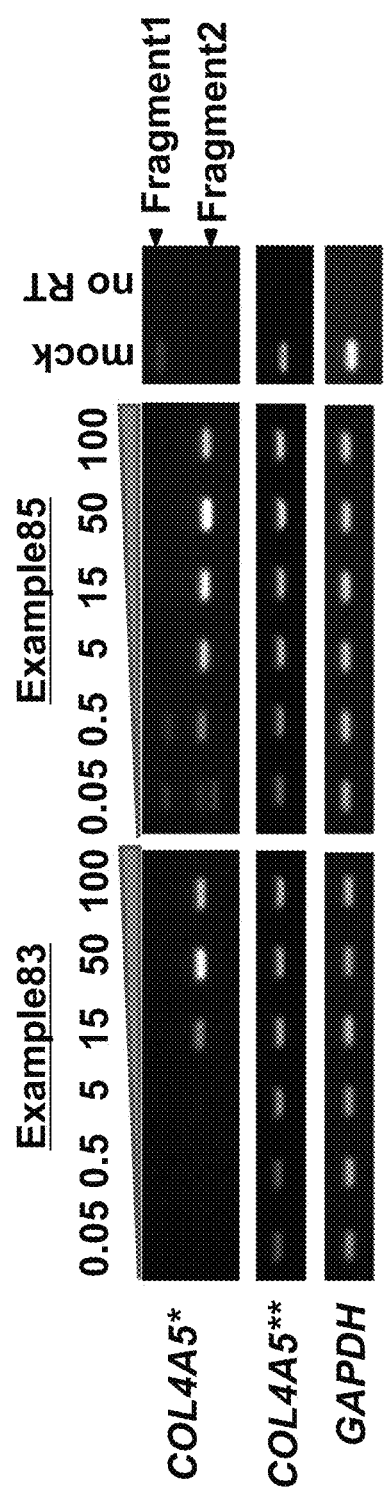
FIG. 11 A drawing showing the effects of compounds from Examples 83 and 85 on exon 24 of COL4A5.

As shown in FIG. 11, urine exfoliated cells derived from an Alport syndrome patient with a mutation in exon 24 were differentiated into COL4A5 expressing renal glomerular epithelial cells (podocytes); and exon 24-targeting oligonucleotides (from Examples 83 and 85) were introduced at 0.05, 0.5, 5, 15, 50 or 100 nM each, followed by examination of exon 24 skipping. As a result, skipping of exon 24 was observed with every oligonucleotide in a concentration dependent manner.

Figure 12:
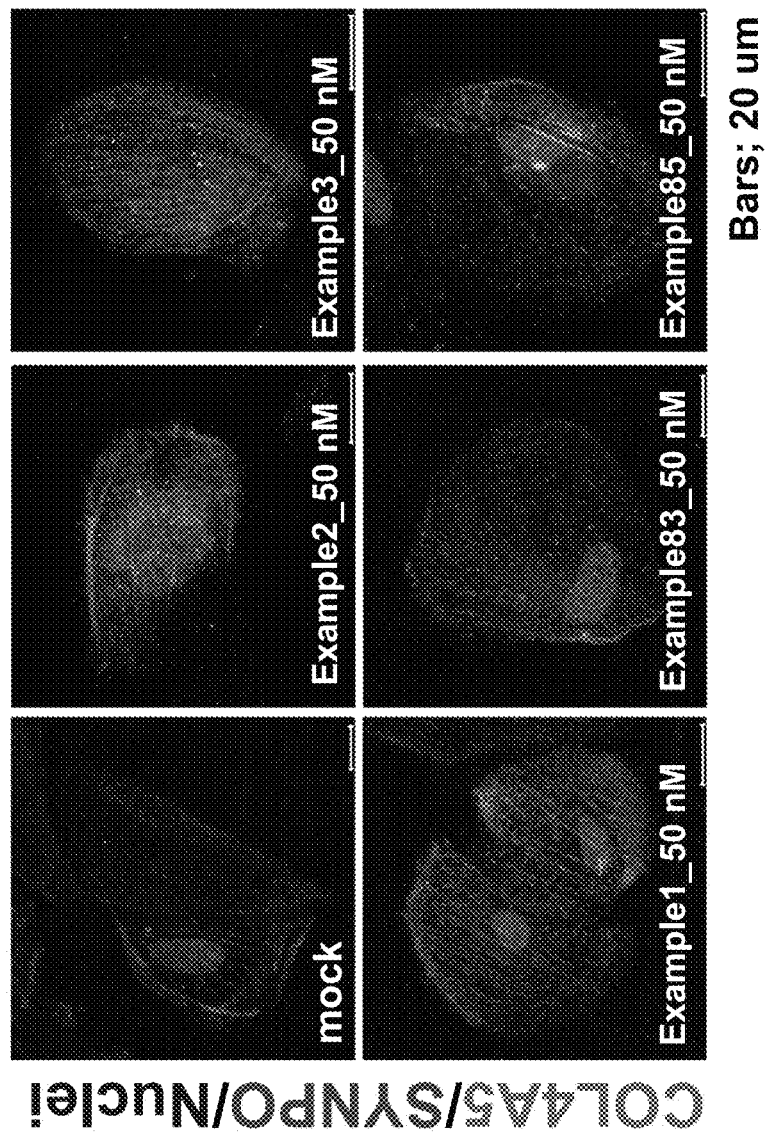
FIG. 12 Drawings showing increases in expressions of COL4A5 protein (green) and Synaptopodin (red) when oligonucleotides targeting exon 24 (from Examples 1 to 3, 83 and 85) were introduced into renal glomerular epithelial cells (podocytes).

As shown in FIG. 12, urine exfoliated cells derived from an Alport syndrome patient with a mutation in exon 24 were differentiated into COL4A5 expressing renal glomerular epithelial cells (podocytes); and exon 24-targeting five oligonucleotides (from Examples 1, 2, 3, 83 and 85) were introduced at 50 nM each, followed by confirmation of their effects. Briefly, expressions of COL4A5 and a differentiated podocyte marker, Synaptopodin (goat anti-Synaptopodin antibody; Santa Cruz) were evaluated. Compared to non-transfected cells (Mock), expression of COL4A5 protein (green) was increased in oligonucleotide-transfected cells. Moreover, an increase in expression of the differentiated podocyte marker Synaptopodin (red) was also confirmed. These results suggested that the introduction of oligonucleotides not only contributes to increased expression of COL4A5 protein but possibly also affects the differentiation capacity of podocytes.

Test Example 3

Analysis of the Exon Skipping Induction Capacity of ENA Oligonucleotide
Culture of HEK293A (a Cell Line Derived from Human Embryonic Kidney Cells)
HEK293A was cultured as described below.
HEK293A (Invitrogen) was cultured in a maintenance medium (DMEM; Thermo Scientific; containing 10% fetal bovine serum (Thermo Scientific)) in 10 cm dish or T75 flask. Immediately before transfection, cells were peeled off with TrypLE Express (Thermo Scientific) to prepare a cell suspension. Oligonucleotides prepared in Examples were introduced by the reverse transfection method as described later.
Transfection of Oligonucleotides Prepared in Examples
Oligonucleotides prepared in Examples were transfected as described below.
The following Solution A and Solution B were prepared and mixed

| Solution A: | Opti-MEM Medium (Thermofisher) | 4.8 µl |
| | Compound prepared in Example (10 µM) | 0.5 µl (final concentration: 50 nM) |
| Solution B: | Opti-MEM Medium | 5 µl |
| | Lipofectamine RNAiMAX (Thermofisher) | 0.3 µl |

The above mixed solution was incubated for 15 min at room temperature. The thus prepared solution was added to 96 well plates in portions of 10.6 µl/well. Then, cells were seeded on these plates at a density of $2\times10^4$ cells/well, followed by incubation for 24 hrs.
RNA Extraction
RNA was extracted as described below.
The cells incubated for 24 hrs after oligonucleotide transfection were washed once with cold PBS. The cell lysis solution contained in SuperPrep Cell Lysis Kit & RT Kit for qPCR (TOYOBO) was added in portions of 50 µl/well. After shaking for 30 sec, cells were incubated at room temperature for 5 min. The quenching solution contained in SuperPrep Cell Lysis Kit & RT Kit for qPCR was added in portions of 10 µl/well. After shaking for 30 sec, cells were incubated at room temperature for 2 min. A total of 60 µl of cell lysate was recovered and used in the reverse transcription reaction described below.
Reverse Transcription Reaction
Reverse transcription was performed as described below.
The reverse transcription master mix (32 µl) and the cell lysis solution (8 µl) both contained in SuperPrep Cell Lysis Kit & RT Kit for qPCR were mixed. Reverse transcription was performed as follows: 37° C. 15 min, 50° C. 5 min, 98° C. 5 min and 4° C. hold. The final products were stored at −20° C.
PCR Reaction and Analysis of Fragment Sequences
PCR reaction and analysis of fragment sequences were performed as described below.
PCR reaction solution was prepared from the components listed below.

| Reverse transcription products | 3 µl |
| Sterilized water | 38.4 µl |
| 10x High Fidelity PCR Buffer (attached to Platinum Taq High Fidelity) | 5 µl |
| 50 mM $MgSO_4$ (attached to Platinum Taq High Fidelity) | 2 µl |
| dNTP (Thermo Scientific) | 1 µl |
| Forward primer (100 µM) | 0.2 µl |
| Reverse primer (100 µM) | 0.2 µl |
| Platinum Taq High Fidelity (Thermo Scientific) | 0.2 µl |
| Total | 50 µl |

PCR reaction was performed as follows: 94° C. 2 min, (94° C. 30 sec, 55° C. 30 sec, 68° C. 1 min)×30-40 cycles, 68° C. 10 min, and 4° C. hold.
Primers for analysis were designed as follows.

```
1) For analysis of skipping of COL4A5 exon 21
(Exon 20-23)
Forward (5'-3'):
                                         (SEQ ID NO: 45)
cagttatgggtcctcctggc Reverse (5'-3'):
                                         (SEQ ID NO: 46)
agttgcaccagcttgtcctt 2) For analysis of endogenous control gene
(ACTB)
Forward (5'-3'):
                                         (SEQ ID NO: 47)
tggcacccagcacaatgaa Reverse (5'-3'):
                                         (SEQ ID NO: 48)
ctaagtcatagtccgcctagaagca
```

Figure 13A:
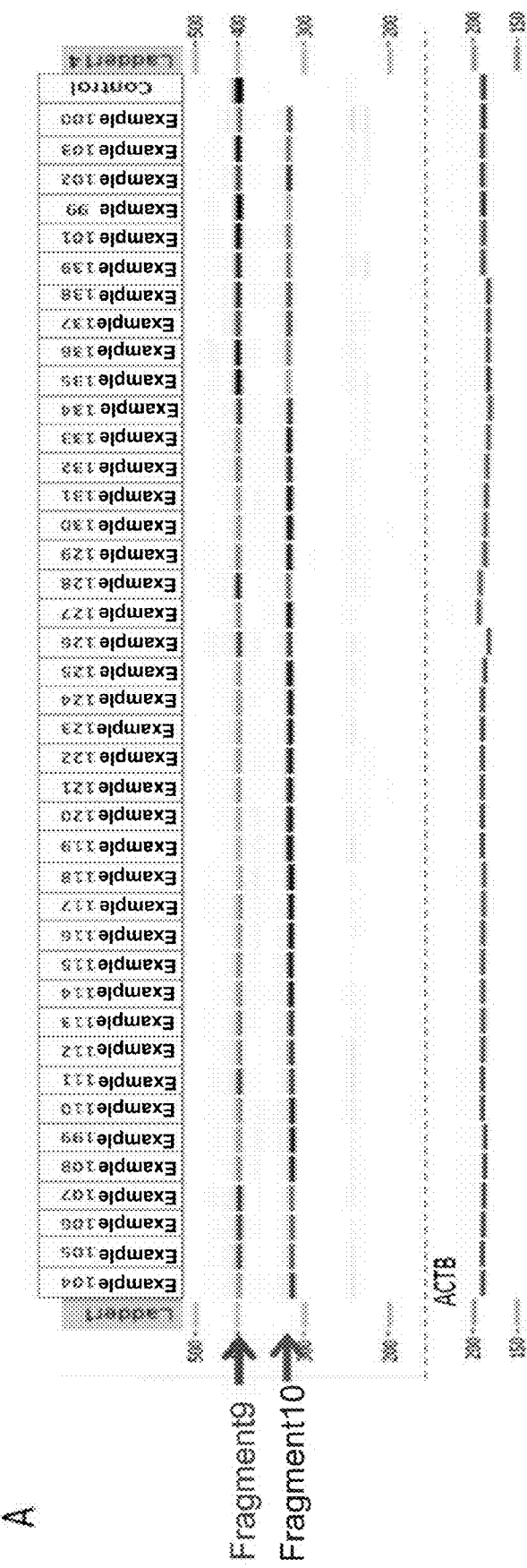
FIG. 13A (A) A drawing showing the effects of compounds from Examples 99 to 139 on exon 21 of COL4A5.

PCR products were analyzed with LabChip™ GX (Caliper LifeSciences). Further, PCR products were electrophoresed in 2% agarose gel containing ethidium bromide and extracted from the gel with NucleoSpin™ Gel and PCR Clean-up (MACHEREY-NAGEL). Extracted DNA was subjected to sequencing with BigDye™ Terminator v3.1. The nucleotide sequence was confirmed with Applied Biosystems 3730x1 DNA Analyzer (Life Technologies).
Exon Skipping Caused by Compounds of Examples in HEK293A
As shown in FIG. 13, when skipping of exon 21 by exon 21-targeting oligonucleotides (from Examples 99 to 139) was examined in HEK293A, skipping of exon 21 was confirmed with every one of the oligonucleotides examined (FIG. 13A). Further, from the results of sequence analysis of fragments extracted from the gel, it was confirmed that fragment 9 had the sequence before skipping whereas fragment 10 had a sequence involving the skipping of exon 21 (FIGS. 13B and 13C).

Test Example 4

Analysis of the Exon Skipping Induction Capacity of ENA Oligonucleotide

Culture of HMVECs (human dermal microvascular endothelial cells), preparation of a primary culture system for urine exfoliated cells, directed differentiation into renal glomerular epithelial cells (podocytes), transfection of oligonucleotides prepared in Examples, RNA extraction, reverse transcription reaction, PCR reaction and sequence analysis of fragments, and immunofluorescent staining of differentiated podocytes were carried out in the same manner as described in Test Example 1.

However, primers for analysis were designed as follows.

```
Primers for analysis of exon 21 skipping (Exon
18-24)
Forward (5'-3'):
                                      (SEQ ID NO: 49)
GACCTCCTGGACTTGTAATTCCTA Reverse (5'-3'):
                                      (SEQ ID NO: 50)
CTCCTGGAATGCCTGGTAATCCT
```

Exon Skipping Caused by the Compounds of Examples, in HMVEC or Alport Syndrome Patient-Derived Urine Exfoliated Cells As shown in FIG. 14A, when skipping of exon 21 by exon 21-targeting oligonucleotides (from Examples 99 to 139) was examined in HMVEC, skipping of exon 21 was observed with every one of the oligonucleotides tested. Further, from the results of sequence analysis of the fragments shown in the gel, fragment 11 was confirmed to have a sequence involving the skipping of exon 20 (FIGS. 14B and 14C). Exon 21-targeting oligonucleotides were used to give a final concentration of 5 nM.

Figure 15:
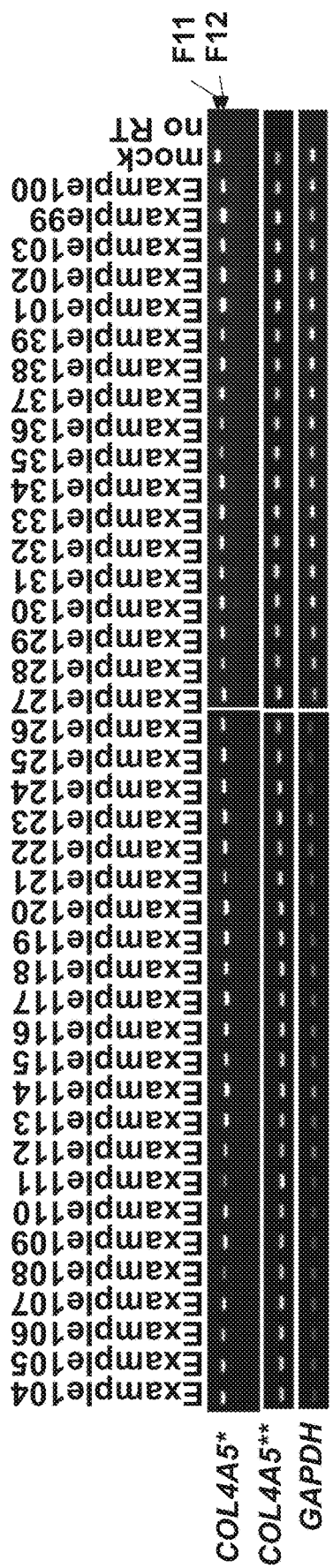
FIG. 15 A drawing showing the effects of compounds from Examples 99 to 139 on exon 21 of COL4A5.

As shown in FIG. 15, urine exfoliated cells derived from an Alport syndrome patient with a mutation in exon 21 were differentiated into COL4A5 expressing renal glomerular epithelial cells (podocytes); and exon 21 skipping by exon 21-targeting oligonucleotides (from Examples 99 and 139) was examined. As a result, skipping of exon 21 was observed with every one of the oligonucleotides tested. Exon 21-targeting oligonucleotides were used to give a final concentration of 50 nM.

Figure 16:
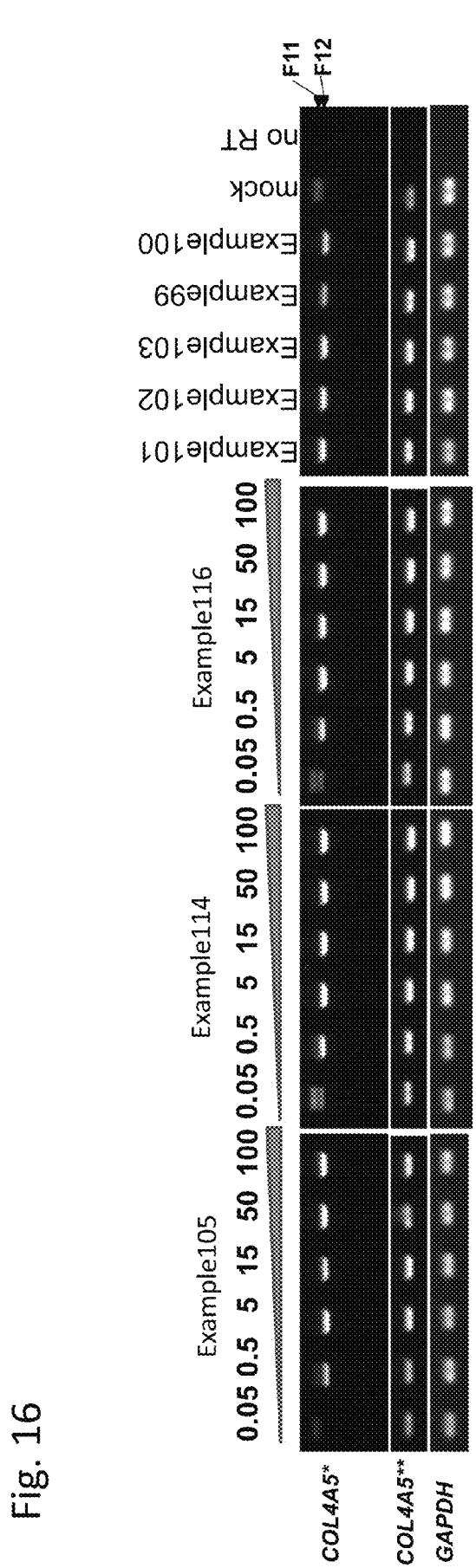
FIG. 16 A drawing showing the effects of compounds from Examples 105, 114 and 116 on exon 21 of COL4A5.

As shown in FIG. 16, urine exfoliated cells derived from an Alport syndrome patient with a mutation in exon 21 were differentiated into COL4A5 expressing renal glomerular epithelial cells (podocytes); and exon 21-targeting oligonucleotides (from Examples 105, 114 and 116) were introduced at 0.05, 0.5, 5, 15, 50 or 100 nM each, followed by examination of exon 21 skipping. As a result, skipping of exon 21 was observed with every oligonucleotide in a concentration dependent manner.

Figure 17:
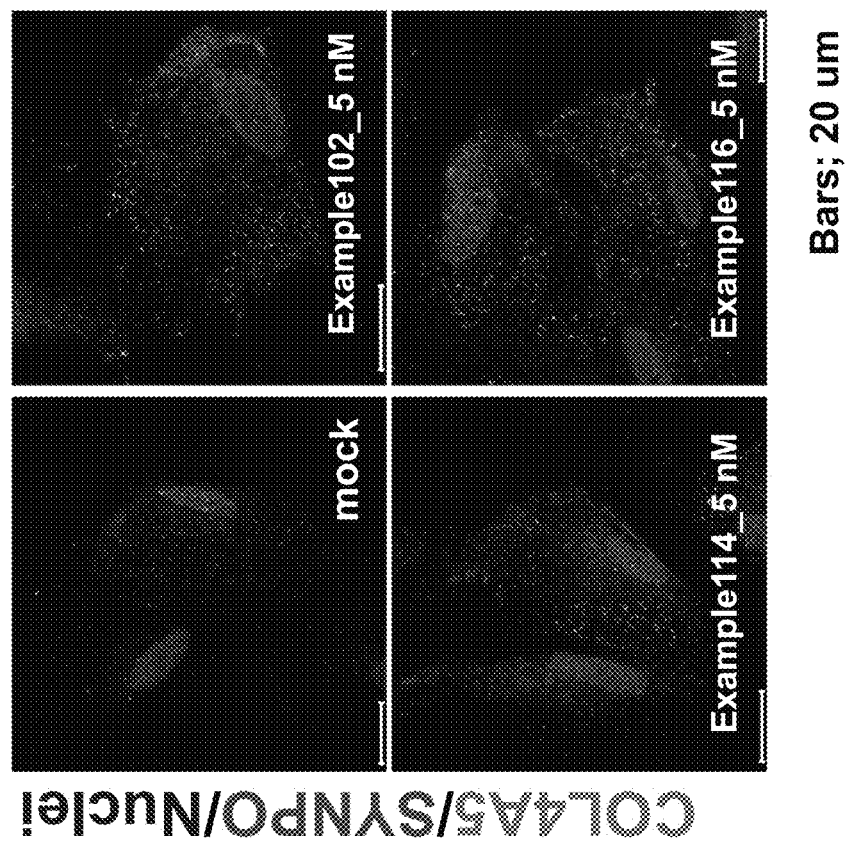
FIG. 17 Drawings showing increases in expressions of COL4A5 protein (green) and Synaptopodin (red) when oligonucleotides targeting exon 21 (from Examples 102, 114 and 116) were introduced into renal glomerular epithelial cells (podocytes).

As shown in FIG. 17, urine exfoliated cells derived from an Alport syndrome patient with a mutation in exon 21 were differentiated into COL4A5 expressing renal glomerular epithelial cells (podocytes); and exon 21-targeting three oligonucleotides (from Examples 102, 105, 114 and 116) were introduced at 5 nM each, followed by confirmation of their effects. Briefly, expressions of COL4A5 and a differentiated podocyte marker Synaptopodin (goat anti-Synaptopodin antibody; Santa Cruz) were evaluated. Compared to non-transfected cells (Mock), expression of COL4A5 protein (green) was increased in the oligonucleotide-transfected cells. Moreover, an increase in expression of the differentiated podocyte marker Synaptopodin (red) was also confirmed. These results suggested that the introduction of oligonucleotide not only contributes to increased expression of COL4A5 protein but possibly also affects the differentiation capacity of podocytes.

Examples 140 and 141

Compounds of Examples 140 and 141 were also synthesized in the same manner as described in Example 4. The sequences and data of compounds from Examples 140 and 141 are summarized in Table 7 below.

TABLE 7

| Example | Designation | Sequence (5'-3') | Start | End | Molecular Weight | SEQ ID NO: |
|---|---|---|---|---|---|---|
| 140 | ex21_012-2 | TccTuuAucAccTgg | 156696 | 156682 | 5183.57 | 51 |
| 141 | ex21_012-4 | cTuuAucAccTggAg | 156694 | 156680 | 5232.56 | 52 |

In sequences shown in the Table, capital letters represent ENA and small letters 2'-OMe-RNA. For "Start" and "End", respective nucleotide numbers in *Homo sapiens* collagen type IV alpha 5 chain (COL4A5) (NCBI-GenBank accession No. NG_011977) are shown. Molecular weights in the Table show values as measured by negative-ion ESI mass spectrometry.

Example 142

(SEQ ID NO: 44)
HO-$T^{els}$-$G^{mls}$-$G^{mls}$-$A^{els}$-$G^{mls}$-$U^{mls}$-$C^{mls}$-$C^{mls}$-$U^{mls}$-$U^{mls}$-$U^{mls}$-$A^{els}$-$U^{mls}$-$C^{mls}$-$A^{els}$-$C^{mls}$-$C^{mls}$-$T^{lt}$-H (ex21_Lc29)

The compound of Example 142 was synthesized by the phosphoramidite method (Nucleic Acids Research, 12, 4539, 1984). The LNA portion was synthesized using the phosphoramidite disclosed in WO99/14226.

When analyzed by reversed phase HPLC [column (X-Bridge C18 2.5 μm (4.6×75 mm); Solution A: an aqueous solution of 100 mM hexafluoroisopropanol (HFIP) and 8 mM triethylamine; Solution B: methanol, B %: from 5% to 30% (20 min, liner gradient); 60° C.; 1 ml/min; 260 m], the subject compound was eluted at 12.87 min. The compound was identified by negative-ion ESI mass spectrometry (found: 6173.88).

The nucleotide sequence of the subject compound is a sequence complementary to nucleotide Nos. 156701 to 156684 of *Homo sapiens* collagen type IV alpha 5 chain (COL4A5) (NCBI-GenBank accession No. NG_011977).

Examples 143 to 280

Compounds of Examples 143 to 280 can be synthesized in the same manner as described in Example 142. The sequences of compounds from Examples 143 to 280 are summarized in Tables 8 to 11.

TABLE 8

| Example | Designation | Sequence (5'-3') | Start | End | SEQ ID NO: |
|---|---|---|---|---|---|
| 143 | ex21_L010 | cTugGagTccTuuAucAc | 156703 | 156686 | 40 |
| 144 | ex21_L011 | gGagTccTuuAucAccTg | 156700 | 156683 | 41 |
| 145 | ex21_Lb08 | cCuuGgaGucCuuTauCa | 156704 | 156687 | 42 |
| 146 | ex21_Lb09 | uTggAguCcuTuaTcaCc | 156702 | 156685 | 43 |
| 147 | ex21_Lb10 | uGgaGucCuuTauCacCu | 156701 | 156684 | 44 |
| 148 | ex21_Lc01 | cCuuggAguccTuuauCa | 156704 | 156687 | 42 |
| 149 | ex21_Lc02 | ccTuggAguccTuuaTca | 156704 | 156687 | 42 |
| 150 | ex21_Lc03 | ccuTggAguccTuuAuca | 156704 | 156687 | 42 |
| 151 | ex21_Lc04 | ccTuggagTccuTuaTca | 156704 | 156687 | 42 |
| 152 | ex21_Lc05 | CcTuggagTccuuuaTcA | 156704 | 156687 | 42 |
| 153 | ex21_Lc06 | CcTuggaguCcuuuaTcA | 156704 | 156687 | 42 |
| 154 | ex21_Lc07 | CcTuggagucCuuuaTcA | 156704 | 156687 | 42 |
| 155 | ex21_Lc08 | cCuTggagTccuuuAuCa | 156704 | 156687 | 42 |
| 156 | ex21_Lc09 | cCuTggaguCcuuuAuCa | 156704 | 156687 | 42 |
| 157 | ex21_Lc10 | cTuggAguccuuTaucAc | 156703 | 156686 | 40 |
| 158 | ex21_Lc12 | CuTggaguCcuuuauCaC | 156703 | 156686 | 40 |
| 159 | ex21_Lc13 | CuTggagucCuuuauCaC | 156703 | 156686 | 40 |
| 160 | ex21_Lc14 | CuTggaguccTuuauCaC | 156703 | 156686 | 40 |
| 161 | ex21_Lc15 | uTggagTccuuTaucaCc | 156702 | 156685 | 43 |
| 162 | ex21_Lc16 | uTggAguccuuuaTcaCc | 156702 | 156685 | 43 |
| 163 | ex21_Lc17 | TuggAgucCuuuaTcacC | 156702 | 156685 | 43 |
| 164 | ex21_Lc18 | TuggAguccTuuaTcacC | 156702 | 156685 | 43 |
| 165 | ex21_Lc19 | uTggAgucCuuuaTcaCc | 156702 | 156685 | 43 |
| 166 | ex21_Lc20 | uTggAguccTuuaTcaCc | 156702 | 156685 | 43 |
| 167 | ex21_Lc21 | uTggagTcCruuaTcaCc | 156702 | 156685 | 43 |
| 168 | ex21_Lc22 | uTggagTccuTuaTcaCc | 156702 | 156685 | 43 |
| 169 | ex21_Lc23 | TuggagTccTuuaTcacC | 156702 | 156685 | 43 |
| 170 | ex21_Lc24 | uggAguCcuuuAucAccu | 156701 | 156684 | 44 |
| 171 | ex21_Lc25 | uGgaguCcuuuAucacCu | 156701 | 156684 | 44 |
| 172 | ex21_Lc26 | uggaguCcuuTauCacCu | 156701 | 156684 | 44 |
| 173 | ex21_Lc27 | TggAguccuuuAucAccT | 156701 | 156684 | 44 |
| 174 | ex21_Lc28 | TggAguCcuuuaTcaCcu | 156701 | 156684 | 44 |
| 175 | ex21_Lc30 | TggagucCuuTauCacCu | 156701 | 156684 | 44 |
| 176 | ex21_Lc31 | TggagTccuTuauCaccT | 156701 | 156684 | 44 |
| 177 | ex21_Lc32 | TggagTccuTuauCacCu | 156701 | 156684 | 44 |

TABLE 8-continued

| Example | Designation | Sequence (5'-3') | Start | End | SEQ ID NO: |
|---|---|---|---|---|---|
| 178 | ex21_Lc33 | TggagTccuTuauCacCu | 156701 | 156684 | 44 |
| 179 | ex21_Lc34 | ggAgucCuuuaTcacCug | 156700 | 156683 | 41 |
| 180 | ex21_Lc35 | ggAguCcuuTaucAccTg | 156700 | 156683 | 41 |
| 181 | ex21_Lc36 | gGagucCuuuaTcaccTg | 156700 | 156683 | 41 |
| 182 | ex21_Lc37 | ggAguCcuTuaTcaCcug | 156700 | 156683 | 41 |

In sequences shown in the Table, capital letters represent LNA and small letters 2'-OMe-RNA. For "Start" and "End", respective nucleotide numbers in *Homo sapiens* collagen type IV alpha 5 chain (COL4A5) (NCBI-GenBank accession No. NG_011977) are shown.

TABLE 9

| Example | Designation | Sequence (5'-3') | Start | End | SEQ ID NO: |
|---|---|---|---|---|---|
| 183 | ex24_L011 | cCcuGgcAauCcaTccTg | 162604 | 162621 | 1 |
| 184 | ex24_Lb04 | cCugGcaAucCauCcuGu | 162603 | 162620 | 2 |
| 185 | ex24_Lb05 | cTggCaaTccAucCugTc | 162602 | 162619 | 3 |
| 186 | ex24_Lc01 | cCcTggCaaucCauCcTg | 162604 | 162621 | 1 |
| 187 | ex24_Lc02 | cCcTggCaaucCaucCTg | 162604 | 162621 | 1 |
| 188 | ex24_Lc03 | cCcTggCaaTcCauCcTg | 162604 | 162621 | 1 |
| 189 | ex24_Lc04 | CcCuggCaaTcCauCcTg | 162604 | 162621 | 1 |
| 190 | ex24_Lc05 | cCcTggCaAuCcAuCcTg | 162604 | 162621 | 1 |
| 191 | ex24_Lc06 | cCcTggCaaTcCaTeCTg | 162604 | 162621 | 1 |
| 192 | ex24_Lc07 | CCcTggCaaTcCaTeCTg | 162604 | 162621 | 1 |
| 193 | ex24_Lc08 | cCcTgGcAaTcCaTcCuG | 162604 | 162621 | 1 |
| 194 | ex24_Lc09 | cCuggCaaTcCauCcTgu | 162603 | 162620 | 2 |
| 195 | ex24_Lc10 | CcTggCaauccauCcTgT | 162603 | 162620 | 2 |
| 196 | ex24_Lc11 | cCuggCaaTcCauCcTgT | 162603 | 162620 | 2 |
| 197 | ex24_Lc12 | ccTggCaAuCcAuCcTgu | 162603 | 162620 | 2 |
| 198 | ex24_Lc13 | cCTggCaaTcCauCcTgT | 162603 | 162620 | 2 |
| 199 | ex24_Lc14 | CcTggCaAuCcAuCcTgu | 162603 | 162620 | 2 |
| 200 | ex24_Lc15 | cCTggCaaTcCaTCcTgT | 162603 | 162620 | 2 |
| 201 | ex24_Lc16 | CcTggCaAuCcAuCcTgT | 162603 | 162620 | 2 |
| 202 | ex24_Lc17 | cTggCaaTccaTcCugTc | 162602 | 162619 | 3 |
| 203 | ex24_Lc18 | cTggCaauCcaTccTguC | 162602 | 162619 | 3 |
| 204 | ex24_Lc19 | cTggCaaTcCaTcCugTc | 162602 | 162619 | 3 |
| 205 | ex24_Lc20 | CTggCaauCcaTcCugTc | 162602 | 162619 | 3 |
| 206 | ex24_Lc21 | cTggCaAuCcAuCcTgTc | 162602 | 162619 | 3 |
| 207 | ex24_Lc22 | CTggCaaTccAucCugTC | 162602 | 162619 | 3 |

TABLE 9-continued

| Example | Designation | Sequence (5'-3') | Start | End | SEQ ID NO: |
|---|---|---|---|---|---|
| 208 | ex24_Lc23 | CTggCaaTcCaTcCugTC | 162602 | 162619 | 3 |
| 209 | ex24_Lc24 | cTgGcAaTcCaTcCuGuC | 162602 | 162619 | 3 |

In sequences shown in the Table, capital letters represent LNA and small letters 2'-OMe-RNA. For "Start" and "End", respective nucleotide numbers in *Homo sapiens* collagen type IV alpha 5 chain (COL4A5) (NCBI-GenBank accession No. NG_011977) are shown.

TABLE 10

| Example | Designation | Sequence (5'-3') | Start | End | SEQ ID NO: |
|---|---|---|---|---|---|
| 210 | ex24_Lc25 | cCcTggcaaTccauCcTg | 162604 | 162621 | 37 |
| 211 | ex24_Lc26 | CcCuggcaaTccauCcTg | 162604 | 162621 | 37 |
| 212 | ex24_Lc27 | cCcuggCaaTccaTccTg | 162604 | 162621 | 37 |
| 213 | ex24_Lc28 | cCcTggcaauccauCcTg | 162604 | 162621 | 37 |
| 214 | ex24_Lc29 | cCcuggCaaucCaucag | 162604 | 162621 | 37 |
| 215 | ex24_Lc30 | ccCuggCaaucCaucCug | 162604 | 162621 | 37 |
| 216 | ex24_Lc31 | cCcTggcaauccauCcTg | 162604 | 162621 | 37 |
| 217 | ex24_Lc32 | CccuggCaaucCaucag | 162604 | 162621 | 37 |
| 218 | ex24_Lc33 | CcTggcaaTccauccTgT | 162603 | 162620 | 38 |
| 219 | ex24_Lc34 | CcTggcaauCcauccTgT | 162603 | 162620 | 38 |
| 220 | ex24_Lc35 | CcTggcaaucCauccTgT | 162603 | 162620 | 38 |
| 221 | ex24_Lc36 | CcTggcaauccauccTgT | 162603 | 162620 | 38 |
| 222 | ex24_Lc37 | CcuggCaauccaTccugT | 162603 | 162620 | 38 |
| 223 | ex24_Lc38 | ccTggcAauccAuccTgu | 162603 | 162620 | 38 |
| 224 | ex24_Lc39 | ccTggcaaTccaTccugT | 162603 | 162620 | 38 |
| 225 | ex24_Lc40 | cCuggCaauccaTccugT | 162603 | 162620 | 38 |
| 226 | ex24_Lc41 | CuggCaaucCaucCuguC | 162602 | 162619 | 39 |
| 227 | ex24_Lc42 | CuggCaauCcaucCuguC | 162602 | 162619 | 39 |
| 228 | ex24_Lc43 | cTggCaauCcaucCugTc | 162602 | 162619 | 39 |
| 229 | ex24_Lc44 | CuggcAauccauCcuguC | 162602 | 162619 | 39 |
| 230 | ex24_Lc45 | CuggcaAuccaTccuguC | 162602 | 162619 | 39 |
| 231 | ex24_Lc46 | cTggcAauccaTccugTc | 162602 | 162619 | 39 |
| 232 | ex24_Lc47 | cTggcaaTccaTccugTc | 162602 | 162619 | 39 |
| 233 | ex24_Lc48 | cTggcaaTccaucagTc | 162602 | 162619 | 39 |

In sequences shown in the Table, capital letters represent LNA and small letters 2'-OMe-RNA. For "Start" and "End", respective nucleotide numbers in *Homo sapiens* collagen type IV alpha 5 chain (COL4A5) (NCBI-GenBank accession No. NG_011977) are shown.

TABLE 11

| Example | Designation | Sequence (5'-3') | Start | End | SEQ ID NO: |
|---|---|---|---|---|---|
| 234 | ex20_L001 | uAuaGcuTacTagGagGa | 156301 | 156318 | 4 |
| 235 | ex20_L002 | gCuuAcuAggAggAauGu | 156297 | 156314 | 5 |
| 236 | ex20_L022 | gGagGucCagGaaTggAa | 156217 | 156234 | 6 |
| 237 | ex20_L023 | gTccAggAauGgaAauTc | 156213 | 156230 | 7 |
| 238 | ex20_L024 | aGgaAugGaaAuuCcaGg | 156209 | 156226 | 8 |
| 239 | ex20_L044 | uAacTgcAgcCccTaaGa | 156129 | 156146 | 9 |
| 240 | ex20_Lb02 | aAuaTagCuuAcuAggAg | 156303 | 156320 | 10 |
| 241 | ex20_Lb03 | aTauAgcTuaCuaGgaGg | 156302 | 156319 | 11 |
| 242 | ex20_Lb04 | aTagCuuAcuAggAggAa | 156300 | 156317 | 12 |
| 243 | ex20_Lb05 | uAgcTuaCuaGgaGgaAu | 156299 | 156316 | 13 |
| 244 | ex20_Lb07 | cTuaCuaGgaGgaAugTg | 156296 | 156313 | 14 |
| 245 | ex20_Lb09 | uAcuAggAggAauGugAg | 156294 | 156311 | 15 |
| 246 | ex20_Lb10 | gAggTccAggAauGgaAa | 156216 | 156233 | 16 |
| 247 | ex20_Lb11 | aGguCcaGgaAugGaaAu | 156215 | 156232 | 17 |
| 248 | ex20_Lb12 | gGucCagGaaTggAaaTu | 156214 | 156231 | 18 |
| 249 | ex20_Lb13 | uCcaGgaAugGaaAuuCc | 156212 | 156229 | 19 |
| 250 | ex20_Lb14 | cCagGaaTggAaaTucCa | 156211 | 156228 | 20 |
| 251 | ex20_Lb15 | cAggAauGgaAauTccAg | 156210 | 156227 | 21 |
| 252 | ex20_Lb16 | cCauAacTgcAgcCccTa | 156132 | 156149 | 22 |
| 253 | ex20_Lb17 | cAuaAcuGcaGccCcuAa | 156131 | 156148 | 23 |
| 254 | ex20_Lb18 | aTaaCugCagCccCuaAg | 156130 | 156147 | 24 |
| 255 | ex20_Lb19 | aAcuGcaGccCcuAagAu | 156128 | 156145 | 25 |
| 256 | ex20_Lb20 | aCugCagCccCuaAgaTu | 156127 | 156144 | 26 |
| 257 | ex20_Lb21 | cTgcAgcCccTaaGauTc | 156126 | 156143 | 27 |
| 258 | ex20_Lc01 | gTcCaggAaTggaaAuTc | 156213 | 156230 | 28 |
| 259 | ex20_Lc02 | gTcCaggAaTggaaaTuC | 156213 | 156230 | 28 |
| 260 | ex20_Lc03 | gTCcaggaATggaaaTTc | 156213 | 156230 | 28 |
| 261 | ex20_Lc04 | gTccAggAaTggaAauTc | 156213 | 156230 | 28 |
| 262 | ex20_Lc05 | gTcCAggAauggaAauTc | 156213 | 156230 | 28 |
| 263 | ex20_Lc06 | gTccAggAauggaAauTc | 156213 | 156230 | 28 |
| 264 | ex20_Lc07 | gTcCaggaaTggaAauTc | 156213 | 156230 | 28 |
| 265 | ex20_Lc08 | gTccAggaaTggAaaTuc | 156213 | 156230 | 28 |
| 266 | ex20_Lc09 | gTcCaggaauggaAauTc | 156213 | 156230 | 28 |
| 267 | ex20_Lc10 | gTcCaggaauggaaaTuC | 156213 | 156230 | 28 |
| 268 | ex20_Lc11 | gTcCaggaaTggaaauTc | 156213 | 156230 | 28 |

TABLE 11-continued

| Example | Designation | Sequence (5'-3') | Start | End | SEQ ID NO: |
|---|---|---|---|---|---|
| 269 | ex20_Lc12 | uCcAggAaTggAaAuuCc | 156212 | 156229 | 19 |
| 270 | ex20_Lc13 | TccAggAauggAaaTucC | 156212 | 156229 | 19 |
| 271 | ex20_Lc14 | uCcAggaAuggAaAuuCc | 156212 | 156229 | 19 |
| 272 | ex20_Lc15 | uCcAggaAuggAaAuuCc | 156212 | 156229 | 19 |
| 273 | ex20_Lc16 | uCcAggAaTggaaaTuCc | 156212 | 156229 | 19 |
| 274 | ex20_Lc17 | uCcAggAauggAaAuuCc | 156212 | 156229 | 19 |
| 275 | ex20_Lc18 | uCcAggaauggaAaTuCc | 156212 | 156229 | 19 |
| 276 | ex20_Lc19 | TcCaggaaTggaaaTuCc | 156212 | 156229 | 19 |
| 277 | ex20_Lc20 | TcCaggaaTggaaauTcC | 156212 | 156229 | 19 |
| 278 | ex20_Lc21 | uCcAggaauggaaaTuCc | 156212 | 156229 | 19 |
| 279 | ex20_Lc22 | uCcaggAauggAaauuCc | 156212 | 156229 | 19 |
| 280 | ex20_Lc23 | ucCaggAauggAaauTcc | 156212 | 156229 | 19 |

In sequences shown in the Table, capital letters represent LNA and small letters 2'-OMe-RNA. For "Start" and "End", respective nucleotide numbers in *Homo sapiens* collagen type IV alpha 5 chain (COL4A5) (NCBI-GenBank accession No. NG_011977) are shown.

All publications, patents and patent applications cited herein are incorporated herein by reference in their entirety.

INDUSTRIAL APPLICABILITY

The present invention is applicable to treatment of Alport syndrome.

SEQUENCE LISTING FREE TEXT

<SEQ ID NO: 1>
This shows the nucleotide sequence of oligonucleotides (ex24_011, ex24_c01, ex24_c02, ex24_c03, ex24_c04, ex24_c05, ex24_c06, ex24_c07 and ex24_c08) prepared in Examples 1 and 4 to 11.
<SEQ ID NO: 2>
This shows the nucleotide sequence of oligonucleotides (ex24_b04, ex24_c09, ex24_c10, ex24_c11, ex24_c12, ex24_c13, ex24_c14, ex24_c15 and ex24_c16) prepared in Examples 2 and 12 to 19.
<SEQ ID NO: 3>
This shows the nucleotide sequence of oligonucleotides (ex24_b05, ex24_c17, ex24_c18, ex24_c19, ex24_c20, ex24_c21, ex24_c22, ex24_c23 and ex24_c24) prepared in Examples 3 and 20 to 27.
<SEQ ID NO: 4>
This shows the nucleotide sequence of oligonucleotide (ex20_001) prepared in Example 28.
<SEQ ID NO: 5>
This shows the nucleotide sequence of oligonucleotide (ex20_002) prepared in Example 29.
<SEQ ID NO: 6>
This shows the nucleotide sequence of oligonucleotide (ex20_022) prepared in Example 30.
<SEQ ID NO: 7>
This shows the nucleotide sequence of oligonucleotide (ex20_023) prepared in Example 31.
<SEQ ID NO: 8>
This shows the nucleotide sequence of oligonucleotide (ex20_024) prepared in Example 32.
<SEQ ID NO: 9>
This shows the nucleotide sequence of oligonucleotide (ex20_044) prepared in Example 33.
<SEQ ID NO: 10>
This shows the nucleotide sequence of oligonucleotide (ex20_b02) prepared in Example 34.
<SEQ ID NO: 11>
This shows the nucleotide sequence of oligonucleotide (ex20_b03) prepared in Example 35.
<SEQ ID NO: 12>
This shows the nucleotide sequence of oligonucleotide (ex20_b04) prepared in Example 36.
<SEQ ID NO: 13>
This shows the nucleotide sequence of oligonucleotide (ex20_b05) prepared in Example 37.
<SEQ ID NO: 14>
This shows the nucleotide sequence of oligonucleotide (ex20_b07) prepared in Example 38.
<SEQ ID NO: 15>
This shows the nucleotide sequence of oligonucleotide (ex20_b09) prepared in Example 39.
<SEQ ID NO: 16>
This shows the nucleotide sequence of oligonucleotide (ex20_b10) prepared in Example 40.
<SEQ ID NO: 17>
This shows the nucleotide sequence of oligonucleotide (ex20_b11) prepared in Example 41.
<SEQ ID NO: 18>
This shows the nucleotide sequence of oligonucleotide (ex20_b12) prepared in Example 42.
<SEQ ID NO: 19>
This shows the nucleotide sequence of oligonucleotides (ex20_b13, ex20_c12, ex20_c13, ex20_c14, ex20_c15, ex20_c16, ex20_c17, ex20_c18, ex20_c19, ex20_c20, ex20_c21, ex20_c22 and ex20_c23) prepared in Examples 43 and 63 to 74.
<SEQ ID NO: 20>
This shows the nucleotide sequence of oligonucleotide (ex20_b14) prepared in Example 44.

<SEQ ID NO: 21>
This shows the nucleotide sequence of oligonucleotide (ex20_b15) prepared in Example 45.
<SEQ ID NO: 22>
This shows the nucleotide sequence of oligonucleotide (ex20_b16) prepared in Example 46.
<SEQ ID NO: 23>
This shows the nucleotide sequence of oligonucleotide (ex20_b17) prepared in Example 47.
<SEQ ID NO: 24>
This shows the nucleotide sequence of oligonucleotide (ex20_b18) prepared in Example 48.
<SEQ ID NO: 25>
This shows the nucleotide sequence of oligonucleotide (ex20_b19) prepared in Example 49.
<SEQ ID NO: 26>
This shows the nucleotide sequence of oligonucleotide (ex20_b20) prepared in Example 50.
<SEQ ID NO: 27>
This shows the nucleotide sequence of oligonucleotide (ex20_b21) prepared in Example 51.
<SEQ ID NO: 28>
This shows the nucleotide sequence of oligonucleotides (ex20_c01, ex20_c02, ex20_c03, ex20_c04, ex20_c05, ex20_c06, ex20_c07, ex20_c08, ex20_c09, ex20_c10 and ex20_c11) prepared in Examples 52 to 62.
<SEQ ID NO: 29>
This shows the nucleotide sequence of (Exon 1-7) forward (5'-3') primer for analysis of the expression of entire COL4A5.
<SEQ ID NO: 30>
This shows the nucleotide sequence of (Exon 1-7) reverse (5'-3') primer for analysis of the expression of entire COL4A5.
<SEQ ID NO: 31>
This shows the nucleotide sequence of (Exon 17-22) forward (5'-3') primer for analysis of COL4A5 exon 20 skipping.
<SEQ ID NO: 32>
This shows the nucleotide sequence of (Exon 17-22) reverse (5'-3') primer for analysis of COL4A5 exon 20 skipping.
<SEQ ID NO: 33>
This shows the nucleotide sequence of (Exon 21-26) forward (5'-3') primer for analysis of COL4A5 exon 24 skipping.
<SEQ ID NO: 34>
This shows the nucleotide sequence of (Exon 21-26) reverse (5'-3') primer for analysis of COL4A5 exon 24 skipping.
<SEQ ID NO: 35>
This shows the nucleotide sequence of forward (5'-3') primer for analysis of an endogenous control gene (GAPDH).
<SEQ ID NO: 36>
This shows the nucleotide sequence of reverse (5'-3') primer for analysis of an endogenous control gene (GAPDH).
<SEQ ID NO: 37>
This shows the nucleotide sequence of oligonucleotides (ex24_c25, ex24_c26, ex24_c27, ex24_c28, ex24_c29, ex24_c30, ex24_c31 and ex24_c32) prepared in Examples 75 to 82.

<SEQ ID NO: 38>
This shows the nucleotide sequence of oligonucleotides (ex24_c33, ex24_c34, ex24_c35, ex24_c36, ex24_c37, ex24_c38 and ex24_c39) prepared in Examples 83 to 90.
<SEQ ID NO: 39>
This shows the nucleotide sequence of oligonucleotides (ex24_c41, ex24_c42, ex24_c43, ex24_c44, ex24_c45, ex24_c46, ex24_c47 and ex24_c48) prepared in Examples 91 to 98.
<SEQ ID NO: 40>
This shows the nucleotide sequence of oligonucleotides (ex21_010, ex21_c10, ex21_c12, ex21_c13 and ex21_c14) prepared in Examples 99 and 113 to 116.
<SEQ ID NO: 41>
This shows the nucleotide sequence of oligonucleotides (ex21_011, ex21_c34, ex21_c35, ex21_c36 and ex21_c37) prepared in Examples 100 and 136 to 139.
<SEQ ID NO: 42>
This shows the nucleotide sequence of oligonucleotides (ex21_b08, ex21_c01, ex21_c02, ex21_c03, ex21_c04, ex21_c05, ex21_c06, ex21_c07, ex21_c08 and ex21_c09) prepared in Examples 101 and 104 to 112.
<SEQ ID NO: 43>
This shows the nucleotide sequence of oligonucleotides (ex21_b09, ex21_c15, ex21_c16, ex21_c17, ex21_c18, ex21_c19, ex21_c20, ex21_c21, ex21_c22 and ex21_c23) prepared in Examples 102 and 117 to 125.
<SEQ ID NO: 44>
This shows the nucleotide sequence of oligonucleotides ((ex21_b10, ex21_c24, ex21_c25, ex21_c26, ex21_c27, ex21_c28, ex21_c29, ex21_c30, ex21_c31, ex21_c32 and ex21_c33) prepared in Examples 103 and 126 to 135.
<SEQ ID NO: 45>
This shows the nucleotide sequence of (Exon 20-23) forward (5'-3') primer for analysis of COL4A5 exon 21 skipping.
<SEQ ID NO: 46>
This shows the nucleotide sequence of (Exon 20-23) reverse (5'-3') primer for analysis of COL4A5 exon 21 skipping.
<SEQ ID NO: 47>
This shows the nucleotide sequence of forward (5'-3') primer for analysis of an endogenous control gene (ACTB).
<SEQ ID NO: 48>
This shows the nucleotide sequence of reverse (5'-3') primer for analysis of an endogenous control gene (ACTB).
<SEQ ID NO: 49>
This shows the nucleotide sequence of (Exon 18-24) forward (5'-3') primer for analysis of COL4A5 exon 21 skipping.
<SEQ ID NO: 50>
This shows the nucleotide sequence of (Exon 18-24) reverse (5'-3') primer for analysis of COL4A5 exon 21 skipping.
<SEQ ID NO: 51>
This shows the nucleotide sequence of oligonucleotide (ex21_012-2) prepared in Example 140.
<SEQ ID NO: 52>
This shows the nucleotide sequence of oligonucleotide (ex21_012-4) prepared in Example 141.

The invention claimed is:

1. An oligonucleotide of 15-30 bases comprising a nucleotide sequence complementary to an exon sequence of the COL4A5 gene,
   wherein the exon is exon 20, 21 or 24 of the COL4A5 gene, wherein the sequence of the exon comprises a truncating mutation, and
   wherein the oligonucleotide induces skipping of the exon during expression of the COL4A5 gene,
   wherein at least one of the sugars and/or at least one of the phosphodiester bonds constituting the oligonucleotide is modified, and
   a pharmaceutically acceptable salt thereof, or a solvate thereof.

2. The oligonucleotide of claim 1, comprising the whole or part of any of the sequences as shown in SEQ ID NOS: 1 to 28, 37 to 44, 51 and 52 wherein the nucleotides "t" may be "u", and "u" may be "t".

3. The oligonucleotide of claim 1, wherein a sugar constituting the oligonucleotide is D-ribofuranose and a modification of the sugar is a modification of the hydroxy group at 2'-position of D-ribofuranose.

4. The oligonucleotide of claim 3, wherein a modification of the sugar is 2'-O-alkylation and/or 2'-O, 4'-C-alkylenation of D-ribofuranose.

5. The oligonucleotide of claim 1, wherein a modification of a phosphodiester bond is replacement of a phosphodiester bond with a phosphorothioate bond.

6. The oligonucleotide of claim 1, wherein the oligonucleotide has a sequence of any one of SEQ ID NOS: 1, 2, 3, 7, 12, 15, 19, 24, 25, 28, 38, 41, 43 and 44, wherein the nucleotides "t" may be "u", and "u" may be "t".

7. The oligonucleotide of claim 1, having any one of the following sequences:
   gTccAggAauGgaAauTc (ex20_023) (SEQ ID NO:7),
   aTagCuuAcuAggAggAa (ex20_b04) (SEQ ID NO:12),
   uAcuAggAggAauGugAg (ex20_b09) (SEQ ID NO:18),
   uCcaGgaAugGaaAuuCc (ex20_b13) (SEQ ID NO:19),
   aTaaCugCagCccCuaAg (ex20_b18) (SEQ ID NO:24),
   aAcuGcaGccCcuAagAu (ex20_b19) (SEQ ID NO:25),
   gTccAggAauggaAauTc (ex20_c05) (SEQ ID NO:7),
   TcCaggaaTggaaauTcC (ex20_c20) (SEQ ID NO:58) and
   uCcaggAauggAaauuCc (ex20_c22) (SEQ ID NO:19),
   wherein capital letters represent ENA and small letters represent 2'-OMe-RNA, and each internucleoside bond is a phosphorothioate bond.

8. The oligonucleotide of claim 1, having any one of the following sequences:
   gGagTccTuuAucAccTg (ex21_011) (SEQ ID NO:41),
   uTggAguCcuTuaTcaCc (ex21_b09) (SEQ ID NO:43),
   uGgaGucCuuTauCacCu (ex21_b10) (SEQ ID NO:44),
   uTggagTccuuTaucaCc (ex21_c15) (SEQ ID NO:59),
   uTggAguccTuuaTcaCc (ex21_c20) (SEQ ID NO:43),
   uTggagTccuTuaTcaCc (ex21_c22) (SEQ ID NO:60) and
   TggAguccuuuAucAccT (ex21_c29) (SEQ ID NO:61),
   wherein capital letters represent ENA and small letters represent 2'-OMe-RNA, and each internucleoside bond is a phosphorothioate bond.

9. The oligonucleotide of claim 1, having any one of the following sequences:
   cCcuGgcAauCcaTccTg (ex24_011) (SEQ ID NO:1),
   cCugGcaAucCauCcuGu (ex24_b04) (SEQ ID NO:2),
   cTggCaaTccAucCugTc (ex24_b05) (SEQ ID NO:3),
   CcTggcaaTccauccTgT (ex24_c33) (SEQ ID NO:38),
   CcTggcaauCcauccTgT (ex24_c34) (SEQ ID NO:62) and
   CcTggcaaucCauccTgT (ex24_c35) (SEQ ID NO:62),
   wherein capital letters represent ENA and small letters represent 2'-OMe-RNA, and each internucleoside bond is a phosphorothioate bond.

10. A pharmaceutical drug comprising the oligonucleotide of claim 1, a pharmaceutically acceptable salt thereof, or a solvate thereof.

11. A method of treating Alport syndrome in a subject, comprising administering to a subject in need thereof a pharmaceutically effective amount an oligonucleotide of claim 1, a pharmaceutically acceptable salt thereof, or a solvate thereof.

* * * * *

SEQUENCE LISTING

<160> NUMBER OF SEQ ID NOS: 62

<210> SEQ ID NO 1
<211> LENGTH: 18

```
<212> TYPE: DNA
<213> ORGANISM: Artificial Sequence
<220> FEATURE:
<223> OTHER INFORMATION: Synthetic oligonucleotide

<400> SEQUENCE: 1
cccuggcaau ccatcctg                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 2
ccuggcaauc cauccugu                                                 18

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 3
ctggcaatcc auccgtc                                                  18

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 4
uauagcutac taggagga                                                 18

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
gcuuacuagg aggaaugu                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 6
ggagguccag gaatggaa                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 7
```
gtccaggaau ggaaautc                                          18

<210> SEQ ID NO 8
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 8
aggaauggaa auuccagg                                          18

<210> SEQ ID NO 9
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 9
uaactgcagc ccctaaga                                          18

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 10
aauatagcuu acuaggag                                          18

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11
atauagctua cuaggagg                                          18

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 12
atagcuuacu aggaggaa                                          18

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
uagctuacua ggaggaau                                          18

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 14
ctuacuagga ggaaugtg                                           18

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 15
uacuaggagg aaugugag                                           18

<210> SEQ ID NO 16
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 16
gaggtccagg aauggaaa                                           18

<210> SEQ ID NO 17
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 17
agguccagga auggaaau                                           18

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 18
gguccaggaa tggaaatu                                           18

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 19
uccaggaaug gaaauucc                                           18

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 20
ccaggaatgg aaatucca                                           18

```
<210> SEQ ID NO 21
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 21
caggaaugga aautccag                                                 18

<210> SEQ ID NO 22
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 22
ccauaactgc agcccta                                                  18

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 23
cauaacugca gccccuaa                                                 18

<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 24
ataacugcag ccccuaag                                                 18

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 25
aacugcagcc ccuaagau                                                 18

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 26
acugcagccc cuaagatu                                                 18

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide
```

```
<400> SEQUENCE: 27
ctgcagcccc taagautc                                              18

<210> SEQ ID NO 28
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 28
gtccaggaat ggaaautc                                              18

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
cagaggctgc ggcttgctat                                            20

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
ccacgttctc ccttggttcc a                                          21

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
gggatggtga aagggccaa aaag                                        24

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
cctttgtcac ctttcactcc ttgt                                       24

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
caaggagtga aggtgacaa aggt                                        24

<210> SEQ ID NO 34
```

```
<211> LENGTH: 23
<212> TYPE: DNA
<213> ORGANISM: Artificial Sequence
<220> FEATURE:
<223> OTHER INFORMATION: Primer

<400> SEQUENCE: 34
ccctttagga cctggtattc ctg                                              23

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35
cccttcattg acctcaac                                                    18

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
ttcacaccca tgacgaac                                                    18

<210> SEQ ID NO 37
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 37
ccctggcaat ccaucctg                                                    18

<210> SEQ ID NO 38
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 38
cctggcaatc caucctgt                                                    18

<210> SEQ ID NO 39
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 39
cuggcaaucc auccuguc                                                    18

<210> SEQ ID NO 40
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 40
```

```
ctuggagtcc tuuaucac                                            18

<210> SEQ ID NO 41
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 41
ggagtcctuu aucacctg                                            18

<210> SEQ ID NO 42
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 42
ccuuggaguc cuutauca                                            18

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 43
utggaguccu tuatcacc                                            18

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 44
uggaguccuu taucaccu                                            18

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
cagttatggg tcctcctggc                                          20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
agttgcacca gcttgtcctt                                          20

<210> SEQ ID NO 47
<211> LENGTH: 19
<212> TYPE: DNA
```

```
<213> ORGANISM: Artificial Sequence
<220> FEATURE:
<223> OTHER INFORMATION: Primer

<400> SEQUENCE: 47
tggcacccag cacaatgaa                                                19

<210> SEQ ID NO 48
<211> LENGTH: 25
<212> TYPE: DNA
<213> ORGANISM: Artificial Sequence
<220> FEATURE:
<223> OTHER INFORMATION: Primer

<400> SEQUENCE: 48
ctaagtcata gtccgcctag aagca                                         25

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
gacctcctgg acttgtaatt ccta                                          24

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
ctcctggaat gcctggtaat cct                                           23

<210> SEQ ID NO 51
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 51
tcctuuauca cctgg                                                    15

<210> SEQ ID NO 52
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 52
ctuuaucacc tggag                                                    15

<210> SEQ ID NO 53
<211> LENGTH: 23
<212> TYPE: DNA
<213> ORGANISM: Artificial Sequence
<220> FEATURE:
<223> OTHER INFORMATION: Exons 24 and 25

<400> SEQUENCE: 53
aaggagagcc tggtggaatt act                                           23
```

<210> SEQ ID NO 54
<211> LENGTH: 24
<212> TYPE: DNA
<213> ORGANISM: Artificial Sequence
<220> FEATURE:
<223> OTHER INFORMATION: Exons 23 and 25

<400> SEQUENCE: 54
aaaggattac caggtggaat tact                                              24

<210> SEQ ID NO 55
<211> LENGTH: 21
<212> TYPE: DNA
<213> ORGANISM: Artificial Sequence
<220> FEATURE:
<223> OTHER INFORMATION: Exons 20 and 21

<400> SEQUENCE: 55
attcctccta gtgatgagat a                                                 21

<210> SEQ ID NO 56
<211> LENGTH: 21
<212> TYPE: DNA
<213> ORGANISM: Artificial Sequence
<220> FEATURE:
<223> OTHER INFORMATION: Exons 19 and 21

<400> SEQUENCE: 56
ggacctccag gtgatgagat a                                                 21

<210> SEQ ID NO 57
<211> LENGTH: 18
<212> TYPE: DNA
<213> ORGANISM: Artificial Sequence
<220> FEATURE:
<223> OTHER INFORMATION: Exons 20 and 22

<400> SEQUENCE: 57
attcctccta gtgacaaa                                                     18

<210> SEQ ID NO 58
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 58
tccaggaatg gaaautcc                                                     18

<210> SEQ ID NO 59
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 59
utggagtccu utaucacc                                                     18

<210> SEQ ID NO 60
<211> LENGTH: 18
<212> TYPE: DNA
<213> ORGANISM: Artificial Sequence
<220> FEATURE:

```
<223> OTHER INFORMATION: Synthetic oligonucleotide

<400> SEQUENCE: 60
utggagtccu tuatcacc                                               18

<210> SEQ ID NO 61
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 61
tggaguccuu uaucacct                                               18

<210> SEQ ID NO 62
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 62
cctggcaauc caucctgt                                               18
```